(12) United States Patent
Sordillo

(10) Patent No.: US 11,813,356 B2
(45) Date of Patent: Nov. 14, 2023

(54) DOSING REGIMENS FOR TREATMENT OF PROLIFERATIVE DISORDERS

(71) Applicant: Signpath Pharma, Inc., Sandy, UT (US)

(72) Inventor: Peter Sordillo, New York, NY (US)

(73) Assignee: Signpath Pharma, Inc., Sandy, UT (US)

( * ) Notice: Subject to any disclaimer, the term of this patent is extended or adjusted under 35 U.S.C. 154(b) by 69 days.

(21) Appl. No.: 17/045,431

(22) PCT Filed: Mar. 28, 2019

(86) PCT No.: PCT/US2019/024495
§ 371 (c)(1),
(2) Date: Oct. 5, 2020

(87) PCT Pub. No.: WO2019/199469
PCT Pub. Date: Oct. 17, 2019

(65) Prior Publication Data
US 2021/0161815 A1    Jun. 3, 2021

Related U.S. Application Data

(60) Provisional application No. 62/655,095, filed on Apr. 9, 2018.

(51) Int. Cl.
*A61K 9/127* (2006.01)
*A61P 35/04* (2006.01)
*A61K 9/00* (2006.01)
*A61K 31/12* (2006.01)
*A61K 45/06* (2006.01)

(52) U.S. Cl.
CPC ............ *A61K 9/127* (2013.01); *A61K 9/0019* (2013.01); *A61K 31/12* (2013.01); *A61K 45/06* (2013.01); *A61P 35/04* (2018.01)

(58) Field of Classification Search
None
See application file for complete search history.

(56) References Cited

U.S. PATENT DOCUMENTS

| | | | |
|---|---|---|---|
| 8,372,830 B2 | 2/2013 | Liu et al. | |
| 8,747,890 B2 * | 6/2014 | Helson | A61K 45/06 424/497 |
| 8,784,881 B2 * | 7/2014 | Kurzrock | A61P 1/00 424/450 |
| 10,004,687 B2 * | 6/2018 | Kurzrock | A61K 9/1271 |
| 10,182,997 B2 * | 1/2019 | Kurzrock | A61K 9/1272 |
| 10,485,768 B2 * | 11/2019 | Sordillo | A61K 31/4188 |
| 2002/0110586 A1 * | 8/2002 | Madden | A61P 35/00 514/283 |
| 2006/0067998 A1 | 3/2006 | Kurzrock et al. | |
| 2011/0117186 A1 | 5/2011 | Helson | |
| 2011/0160157 A1 * | 6/2011 | Wang | A61P 1/00 514/414 |
| 2013/0337488 A1 | 12/2013 | Helson | |
| 2015/0164878 A1 | 6/2015 | Helson et al. | |
| 2017/0079934 A1 | 3/2017 | Sordillo et al. | |

FOREIGN PATENT DOCUMENTS

| | | |
|---|---|---|
| EP | 3144006 B1 | 6/2020 |
| KR | 1020170019802 | 2/2017 |
| WO | 2014036534 A1 | 3/2014 |
| WO | 2015077640 A1 | 3/2015 |
| WO | 2015095576 A1 | 6/2015 |
| WO | 2019199469 A1 | 10/2019 |

OTHER PUBLICATIONS

Webster et al. (Circulation, vol. 127, 2013, pp. 126-140). (Year: 2013).*
Storka et al (International Journal of Clinical Pharmacology and Therapeutics, 2014 (Year: 2014).*
SignPath Pharma (https://clinicaltrials.gov/ct2/show/study/NCT02138955) (Year: 2014).*
Extended European Search Report dated Nov. 24, 2021 for 19785177.7, 7 pp.
Aziza SA, et al. "Chemopreventive effect of curcumin on oxidative stress, antioxidant status, DNA fragmentation and caspase-9 gene expression in 1, 2-dimethylhydrazine-induced colon cancer in rats," American J Biochem Mol Biol 2014; 4: 22-34.
Barbaryan A,, et al., "Ibuprofen-induced hemolytic anemia," Case Rep Hematol 2013; 142865: 1-3.
Bolger GT, et al., "Distribution and metabolism of Lipocurc™ (liposomal curcumin) in dog and human blood cells: species selectivity and pharmacokinetic relevance," Anticancer Res 2017; 37: 3483-3492.
Chainani-Wu N. Safety and anti-inflammatory activity of curcumin: a component of turmeric (*Curcuma longa*). J Altern Complement Med 2003; 9: 161-168.
Chang YC., et al., "The generation of induced pluripotent stem cells for macular degeneration as a drug screening platform: identification of curcumin as a protective agent for retinal pigment epithelial cells against oxidative stress," Front Aging Neurosci 2014; 6: 191.
Chen F., et al., "Curcumin increased the differentiation rate of neurons in neural stem cells via wnt signaling in vitro study," J Surg Res 2014; 192: 298-304.

(Continued)

*Primary Examiner* — Celeste A Roney
(74) *Attorney, Agent, or Firm* — Edwin S. Flores; Daniel J. Chalker; Chalker Flores, LLP

(57) ABSTRACT

The present invention includes compositions and methods for treating a proliferative disorder comprising administering a therapeutically effective amount of an liposomal curcumin or curcuminoids to a human subject in need thereof in accordance with a dosing regimen comprising: at least one treatment cycle administering the therapeutically effective amount of the liposomal curcumin or curcuminoids once per week of at least 100 mg/m2 over 8 hours.

10 Claims, 4 Drawing Sheets

(56) References Cited

OTHER PUBLICATIONS

Di Pierro F., et al., "Safety and efficacy of an add-on therapy with curcumin phytosome and piperine and/or lipoic acid in subjects with a diagnosis of peripheral neuropathy treated with dexibuprofen," J Pain Res 2013; 6: 497-503.

Greil, Richard, et al., "A phase 1 dose-escalation study on the safety, tolerability and activity of liposomal curcumin (LipocureTM) in patients with locally advanced or metastatic cancer," Cancer Chemotherapy and Pharmacology, vol. 82, Aug. 3, 2018, pp. 695-706.

Han, et al. "Curcumin induces autophagy to protect vascular endothelial cell survival from oxidative stress damage," Autophagy 2012, 8: 812-825.

Helson, L, et al., "Infusion pharmacokinetics of Lipocurc™(liposomal curcumin) and its metabolite tetrahydrocurcumin in Beagle dogs," Anticancer Res. 2012; 32: 4365-4370.

Hua WM, et al., "Mechanisms of curcumin protecting endothelial cells against ischemia and reperfusion injury," Chinese Pharmacol Bull 2009; 8: 13.

International Search Report and Written Opinion by the Australian Patent Office for PCT/US2019/024495 dated Jun. 26, 2019.

Kanai, et al., "A phase I study investigating the safety and pharmacokinetics of highly bioavailable curcumin (Theracurmin®) in cancer patients," Cancer Chemother Pharmacol 2013; 71: 1521-1530.

Khor, et al., G "Combined inhibitory effects of curcumin and phenethyl isothiocyanate on the growth of human PC-3 prostate xenografts in immunodeficient mice," Cancer Res 2006; 66: 613-621.

Kunwar A, et al., "Quantitative cellular uptake, localization and cytotoxicity of curcumin in normal and tumor cells," Biochim Biophys Acta-General Subjects 2008; 1780: 673-679.

Li, L., et al., "Liposome-encapsulated curcumin: in vitro and in vivo effects on proliferation, apoptosis, signaling, and angiogenesis," Cancer 2005; 104: 1322-1331.

Li, L., et al. "Liposomal curcumin with and without oxaliplatin: effects on cell growth, apoptosis, and angiogenesis in colorectal cancer," Mol Cancer Ther 2007; 6: 1276-1282.

Mach, CM, et al., "Determination of minimum effective dose and optimal dosing schedule for liposomal curcumin in a xenograft human pancreatic cancer model," Anticancer Res 2009; 29: 1895-1899.

Manrique-Moreno, M. et al., "Human cells and cell membrane molecular models are affected in vitro by the nonsteroidal anti-inflammatory drug ibuprofen," Biochim Biophys Acta—Biomembranes 2011; 1808: 2656-2664.

Matabdul, D., et al., "Tissue distribution of (Lipocurc™) liposomal curcumin and tetrahydrocurcumin following two-and eight-hour infusions in beagle dogs," Anticancer Res 2012; 32: 4359-4364.

Perkins, J., "Fatal drug-induced immune hemolytic anemia due to cefotetan; A case study," Asian J Transfu Sci 2008; 2: 20-23.

Pierce, A., et al., "Pathology consultation on drug-induced hemolytic anemia," Am J Clin Pathol 2011; 136: 7-12.

Ranjan, AP, et al., "Efficacy of liposomal curcumin in a human pancreatic tumor xenograft model: inhibition of tumor growth and angiogenesis," Anticancer Res 2013; 33: 3603-3609.

Sharma, RA, et al., "Pharmacokinetics and pharmacodynamics of curcumin. In: Aggarwal BB, Surh Y, Shishodia S (eds). The molecular targets and therapeutic uses of curcumin in health and disease," Springer: Boston, MA, USA, 2007, pp. 453-470.

Sordillo, LA, et al., "Sphingosine kinase inhibitors as maintenance therapy of glioblastoma after ceramide-induced response," Anticancer Res 2016; 36: 2085-2095.

Sordillo, PP, et al., "Curcumin and cancer stem cells: curcumin has asymmetrical effects on cancer and normal stem cells," Anticancer Res 2015; 35: 599-614.

Storka, A., et al. "Safety, tolerability and pharmacokinetics of liposomal curcumin (Lipocurc™) in healthy humans," Int J Clin Pharmacol Therapeut 2015; 53: 54-65.

Storka, A., et al., "Effect of liposomal curcumin on red blood cells in vitro," Anticancer Res 2013; 33: 3629-3634.

Storka, A., et al., "Safety and pharmacokinetics of liposomal curcumin in healty subjects: A randomized placebo controlled double blind first-in human study," (abstract) in: Proceedings of the 104th Annual Meeting of the American Assocation for Cancer Research, Apr. 6-10, 2013, Washington, D.C., AACR: Cancer Res. 2013, vol. 73 (Suppl) Abstract.

Tiwari SK, et al., "Curcumin-loaded nanoparticles potently induce adult neurogenesis and reverse cognitive deficits in Alzheimer's disease model via canonical Wnt/β-catenin pathway," ACS Nano 2013; 8: 76-103.

Wang YJ, et al., "Stability of curcumin in buffer solutions and characterization of its degradation products," J Pharm Biomed Anal 1997; 15: 1867-1876.

Xu Y, et al., "Curcumin reverses impaired hippocampal neurogenesis and increases serotonin receptor 1A mRNA and brain-derived neurotrophic factor expression in chronically stressed rats," Brain Res 2007; 1162: 9-18.

Lee, Y., et al., "Stimuli-responsive liposomes for drug delivery," WIREs Nanomed Nanobiotechnol, vol. 9, Sep./Oct. 2017, 9:e1450, doi: 10.1102wnan. 1450, 41 pp.

Vahed, S.Z., et al., "Liposome-based drug co-delivery systems in cancer cells," Materials Science and Engineering C, vol. 71, Feb. 1, 2017, pp. 1327-1341.

Li, Z. "Developments of the Studies on the Anti-tumor Effects of Curcumin," Chin. J. Clinicians (Electronic Edition), vol. 7, No. 19, Oct. 2013, pp. 8878-8881.

\* cited by examiner

DOSING REGIMENS FOR TREATMENT OF PROLIFERATIVE DISORDERS

CROSS-REFERENCE TO RELATED APPLICATIONS

This application claims priority to and is the National Stage of International Application No. PCT/US2019/024495 filed on Mar. 28, 2019, and also claims priority to U.S. Provisional Application No. 62/655,095 filed on Apr. 9, 2018, the contents of each of which are incorporated by reference herein.

TECHNICAL FIELD OF THE INVENTION

The present invention relates in general to the field of treatment regimens for proliferative diseases, and more particularly, to dosing regimens with liposomal curcumin in patients with locally advanced or metastatic cancer.

BACKGROUND OF THE INVENTION

Without limiting the scope of the invention, its background is described in connection with the use and dosage forms of curcumin, curcuminoids, and active metabolites thereof.

Curcumin has been reported in both tumoral and normal tissues to acts as an antioxidant and contributes towards maintaining the redox potential of cells. Oral administration as an extract of the turmeric plant has been used in traditional medicine for over two thousand years and is reported to be devoid of toxicity and concomitantly systemic therapeutic activity mainly because of water insolubility, intestinal and hepatic inactivation causing negligible bioavailability to tissues beyond the gastrointestinal tract. To overcome these limitations, parenteral intravenous curcumin formulations with liposomes, polymers (n-isopropylacrylamide, N-vinylpyrrolidione and acrylic acid) and polylactic glycolic acid copolymer are being developed.

U.S. Patent Application No. 20060067998, filed by Kurzrock et al., provides compositions and methods for the treatment of cancer, including pancreatic cancer, breast cancer and melanoma, in a human patient. The methods and compositions of the present invention employ curcumin or a curcumin analogue encapsulated in a colloidal drug delivery system, preferably a liposomal drug delivery system. Suitable colloidal drug delivery systems also include nanoparticles, nanocapsules, microparticles or block copolymer micelles. The colloidal drug delivery system encapsulating curcumin or a curcumin analogue is administered parenterally in a pharmaceutically acceptable carrier.

However, what are needed are formulation and dosage regimens that maximize the anti-proliferative activity of curcumin and/or curcuminoids, while minimizing negative side effect.

SUMMARY OF THE INVENTION

In one embodiment, the present invention includes a method of treating a proliferative disorder comprising administering a therapeutically effective amount of an intravenous liposomal curcumin or curcuminoids to a human subject in need thereof in accordance with a dosing regimen comprising: at least one treatment cycle administering the therapeutically effective amount of the liposomal curcumin or curcuminoids of at least 100 mg/m$^2$ over 8 hours or less. In one aspect, the treatment cycle is followed by a rest period of 4, 5, 6, or 7 days during which no liposomes or active agent are administered. In another aspect, the treatment cycle for 2, 3, 4, 5, 6, 7, 8, 9, 10, 11, or 12 consecutive weeks. In another aspect, the liposomal curcumin or curcuminoids is administered at a dose of 125, 150, 200, 250, 300, 350, 400, 450, 500, or 600 mg/m$^2$. In another aspect, the liposomal curcumin or curcuminoids is administered at a dose of 100 to 600 mg/m$^2$, over 2 to 6 hours. In another aspect, the liposomal curcumin or curcuminoids is administered at a dose of 300 to 600 mg/m$^2$, over 2 to 4 hours. In another aspect, the e liposomal curcumin or curcuminoids is administered at a dose of 300 to 600 mg/m$^2$, over 2 or less. In another aspect, the liposomal curcumin or curcuminoids is administered for 2, 3, 4, 5, 6, or 7 hours. In another aspect, the liposomal curcumin or curcuminoids is administered at a dose of at least 300 mg/m$^2$ over 2, 3, 4, 5, 6, 7, or 8 hours. In another aspect, the curcumin or curcuminoids are synthesized curcumin or curcuminoids. In another aspect, the method further comprises providing an effective dose of at least one of: irinotecan, 5-fluorouracil, leucovorin, capecitabine, antracyclins, doxorubicin, dasatinib, imatinib mesylate, lapatinib, nilotinib, sorafenib, sunitinib, trastuzumab, alemtuzumab, bevacizumab, cetuximab, gemtuzumab, panitumumab, rituximab, tositumomab, trastuzumab and combinations thereof. In another aspect, the proliferative disease is a metastatic cancer. In another aspect, the proliferative disease is selected from breast, uterine, cervical, brain, colon, leukemia, cervix, prostate, GI tract, hepatic, melanoma, or pancreatic cancer. In another aspect, the liposome is at least one of comprises 1-Myristoyl-2-Hydroxy-sn-Glycero-3-Phosphocholine (DMPC), 12-Mysteroyl-2-Hydroxy-sn-Glycero-3-[Phospho-rac-(glycerol)] (DMPG), or DMPC/DMPG liposomes. In one aspect, the lysophosphatidylglycerol includes at least one of a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. In another aspect, the liposome prevents pericardial fibrosis, endomyocardial fibrosis, heart failure, hemorrhagic myocardial necrosis, cardiomyopathy, myocarditis, reduction in left ventricular ejection fraction (LVEF), congestive heart failure (CHF), acute coronary disease, hypertension, myocardial infarction, QT prolongation, or pericarditis caused by the active agent. In another aspect, the liposome does not encapsulate the active agent. In another aspect, the liposomal curcumin or curcuminoids are curcumin/curcuminoid:liposome complex, wherein the curcumin comprises between 2 to 9 weight percent of the curcumin/curcuminoid:liposome complex, wherein the curcumin is at least one of natural or synthetic curcumin and wherein the curcumin/curcuminoid:liposome complex has a ratio of curcumin to lipid (weight to weight) of 1:7.5 to 1:10, wherein the lipid combination is selected from: DMPC; DMPC:Chol 9:1; DMPC:DMPG 9:1; DMPC:Chol:DMPG 8:1:1; DPPC:DMPG 9:1; DPPC:Chol:DMPG 8:1:1; DMPC:DSPE-PEG-2000 95:5; DMPC: Chol:DSPE-PEG-2000 90:10:05; DMPC/DMPG 7:3; DPPC/DMPG 7:3; DPPC/DMPG 9:1.

In another embodiment, the present invention includes a method of treating a proliferative disorder comprising administering a therapeutically effective amount of an intravenous liposomal curcumin or analog thereof, to a human subject in need thereof in accordance with a dosing regimen comprising: at least one treatment cycle administering the therapeutically effective amount of the intravenous liposomal curcumin once per week of at least 100 mg/m² over 8 hours. In one aspect, the treatment cycle is followed by a rest period of 4, 5, 6, or 7 days during which no intravenous liposomal curcumin or analog thereof is administered. In another aspect, the treatment cycle for 2, 3, 4, 5, 6, 7, 8, 9, 10, 11, or 12 consecutive weeks. In another aspect, the liposomal curcumin or curcuminoids is administered at a dose of 125, 150, 200, 250, 300, 350, 400, 450, 500, or 600 mg/m². In another aspect, the liposomal curcumin or curcuminoids is administered at a dose of 100 to 600 mg/m², over 2 to 6 hours. In another aspect, the liposomal curcumin or curcuminoids is administered at a dose of 300 to 600 mg/m², over 2 to 4 hours. In another aspect, the liposomal curcumin or curcuminoids is administered at a dose of 300 to 600 mg/m², over 2 or less. In another aspect, the intravenous liposomal curcumin or analog thereof is administered for 2, 3, 4, 5, 6, or 7 hours. In another aspect, the intravenous liposomal curcumin or analog thereof is administered at a dose of at least 300 mg/m² over 2, 3, 4, 5, 6, 7, or 8 hours. In another aspect, the method further comprises providing an effective dose of at least one of: irinotecan, 5-fluorouracil, leucovorin, capecitabine, antracyclins, doxorubicin, dasatinib, imatinib mesylate, lapatinib, nilotinib, sorafenib, sunitinib, trastuzumab, alemtuzumab, bevacizumab, cetuximab, gemtuzumab, panitumumab, rituximab, tositumomab, trastuzumab and combinations thereof. In another aspect, the proliferative disease is a metastatic cancer. In another aspect, the proliferative disease is selected from breast, uterine, cervical, brain, colon, leukemia, cervix, prostate, GI tract, hepatic, melanoma, or pancreatic cancer. In another aspect, the liposome comprises at least one of 1-Myristoyl-2-Hydroxy-sn-Glycero-3-Phosphocholine (DMPC), 12-Mysteroyl-2-Hydroxy-sn-Glycero-3-[Phospho-rac-(glycerol)] (DMPG), or DMPC/DMPG liposomes. In one aspect, the lysophosphatidylglycerol includes at least one of a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. In another aspect, the intravenous liposomal curcumin or analog thereof does not cause pericardial fibrosis, endomyocardial fibrosis, heart failure, hemorrhagic myocardial necrosis, cardiomyopathy, myocarditis, reduction in left ventricular ejection fraction (LVEF), congestive heart failure (CHF), acute coronary disease, hypertension, myocardial infarction, or pericarditis. In another aspect, the liposome does not encapsulate the curcumin or analog thereof. In another aspect, the liposomal curcumin or curcuminoids are curcumin/curcuminoid:liposome complex, wherein the curcumin comprises between 2 to 9 weight percent of the curcumin/curcuminoid:liposome complex, wherein the curcumin is at least one of isolated or synthetic curcumin and wherein the curcumin/curcuminoid:liposome complex has a ratio of curcumin to lipid (weight to weight) of 1:7.5 to 1:10, wherein the lipid combination is selected from: DMPC; DMPC:Chol 9:1; DMPC:DMPG 9:1; DMPC:Chol:DMPG 8:1:1; DPPC:DMPG 9:1; DPPC:Chol:DMPG 8:1:1; DMPC:DSPE-PEG-2000 95:5; DMPC: Chol:DSPE-PEG-2000 90:10:05; DMPC/DMPG 7:3; DPPC/DMPG 7:3; DPPC/DMPG 9:1.

In yet another embodiment, the present invention includes a method for the treatment for a proliferative diseases comprising: administering to a patient in need thereof an effective amount sufficient to reduce or eliminate the proliferative disease of an anti-proliferative liposomal curcumin or curcuminoids, in an amount effective to prevent, reduce or eliminate the proliferative disease of at least 100 mg/m² over 8 hours or less. In one aspect, the administration comprises at least 100 mg/m² over 8 hours. In another aspect, the treatment cycle is followed by a rest period of 4, 5, 6, or 7 days during which no liposomes or active agent are administered. In another aspect, the treatment cycle for 2, 3, 4, 5, 6, 7, 8, 9, 10, 11, or 12 consecutive weeks. In another aspect, the liposomal curcumin or curcuminoids is administered at a dose of 125, 150, 200, 250, 300, 350, 400, 450, 500, or 600 mg/m². In another aspect, the liposomal curcumin or curcuminoids is administered at a dose of 100 to 600 mg/m², over 2 to 6 hours. In another aspect, the liposomal curcumin or curcuminoids is administered at a dose of 300 to 600 mg/m², over 2 to 4 hours. In another aspect, the liposomal curcumin or curcuminoids is administered at a dose of 300 to 600 mg/m², over 2 or less. In another aspect, the active agent is administered for 2, 3, 4, 5, 6, or 7 hours. In another aspect, the active agent is administered at a dose of at least 300 mg/m² over 2, 3, 4, 5, 6, 7, or 8 hours. In another aspect, the method further comprises providing an effective dose of at least one of: irinotecan, 5-fluorouracil, leucovorin, capecitabine, antracyclins, doxorubicin, dasatinib, imatinib mesylate, lapatinib, nilotinib, sorafenib, sunitinib, trastuzumab, alemtuzumab, bevacizumab, cetuximab, gemtuzumab, panitumumab, rituximab, tositumomab, trastuzumab and combinations thereof. In another aspect, the proliferative disease is a metastatic cancer. In another aspect, the proliferative disease is selected from breast, uterine, cervical, brain, colon, leukemia, cervix, prostate, GI tract, hepatic, melanoma, or pancreatic cancer. In another aspect, the liposome is an empty liposome that is at least one of comprises 1-Myristoyl-2-Hydroxy-sn-Glycero-3-Phosphocholine (DMPC), 12-Mysteroyl-2-Hydroxy-sn-Glycero-3- [Phospho-rac-(glycerol)] (DMPG), or DMPC/DMPG liposomes. In one aspect, the lysophosphatidylglycerol includes at least one of a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. In another aspect, the liposome prevents pericardial fibrosis, endomyocardial fibrosis, heart failure, hemorrhagic myocardial necrosis, cardiomyopathy, myocarditis, reduction in left ventricular ejection fraction (LVEF), congestive heart failure (CHF), acute coronary disease, hypertension, myocardial infarction, QT prolongation, or pericarditis caused by the active agent. In another aspect, the liposome does not encapsulate the active agent. In another aspect, the liposomal curcumin or curcuminoids are curcumin/curcuminoid:liposome complex, wherein the curcumin comprises between 2 to 9 weight percent of the curcumin/curcuminoid: liposome complex, wherein the curcumin is at least one of natural or synthetic curcumin and wherein the curcumin/curcuminoid:liposome complex has a ratio of curcumin to lipid (weight to weight) of 1:7.5 to 1:10, wherein the lipid combination is selected from: DMPC; DMPC:Chol 9:1; DMPC:DMPG 9:1; DMPC:Chol:DMPG 8:1:1; DPPC:DMPG 9:1; DPPC:Chol:DMPG 8:1:1; DMPC:DSPE-PEG-2000 95:5; DMPC:Chol:DSPE-PEG-2000 90:10:05; DMPC/DMPG 7:3; DPPC/DMPG 7:3; DPPC/DMPG 9:1.

In another embodiment, the present invention includes a kit comprising: a dose comprising a therapeutically effective amount of an intravenous liposomal curcumin or curcuminoids to a human subject in need thereof in accordance with a dosing regimen comprising: at least one treatment cycle administering the therapeutically effective amount of the liposomal curcumin or curcuminoids of at least 100 mg/m$^2$ over 8 hours or less. In one aspect, the liposomal curcumin or curcuminoids is administered at a dose of 125, 150, 200, 250, 300, 350, 400, 450, 500, or 600 mg/m$^2$. In another aspect, the liposomal curcumin or curcuminoids is administered at a dose of 100 to 600 mg/m$^2$, over 2 to 6 hours. In another aspect, the liposomal curcumin or curcuminoids is administered at a dose of 300 to 600 mg/m$^2$, over 2 to 4 hours. In another aspect, the liposomal curcumin or curcuminoids is administered at a dose of 300 to 600 mg/m$^2$, over 2 or less. In another aspect, the first and second doses are packaged in the same container, and provide a dose for 2, 3, 4, 5, 6, or 7 hours. In another aspect, the first and second doses are packaged in the same container, and provide a dose of at least 300 mg/m$^2$ over 2, 3, 4, 5, 6, 7, or 8 hours. In another aspect, the liposomal curcumin or curcuminoids are curcumin/curcuminoid:liposome complex, wherein the curcumin comprises between 2 to 9 weight percent of the curcumin/curcuminoid:liposome complex, wherein the curcumin is at least one of natural or synthetic curcumin and wherein the curcumin/curcuminoid:liposome complex has a ratio of curcumin to lipid (weight to weight) of 1:7.5 to 1:10, wherein the lipid combination is selected from: DMPC; DMPC:Chol 9:1; DMPC:DMPG 9:1; DMPC:Chol:DMPG 8:1:1; DPPC:DMPG 9:1; DPPC:Chol:DMPG 8:1:1; DMPC: DSPE-PEG-2000 95:5; DMPC: Chol:DSPE-PEG-2000 90:10:05; DMPC/DMPG 7:3; DPPC/DMPG 7:3; DPPC/DMPG 9:1.

BRIEF DESCRIPTION OF THE DRAWINGS

For a more complete understanding of the features and advantages of the present invention, reference is now made to the detailed description of the invention along with the accompanying figures and in which:

FIG. 1A shows the results from patients #17- #27 receiving liposomal curcumin over 8 h. FIG. 1B shows the results from patients #28- #33 receiving liposomal curcumin over 6 h.

FIG. 2A is a graph for all patients with exception to patients #21 because of interruption of infusion. FIG. 2B is a graph for patients with the exclusion of patients #3, #21 and #24. FIG. 2C is a graph that shows the Mean±SD at each infusion rate for data shown in 2B. The infusion rate normalized 2 h curcumin levels were 7.0, 7.6, 9.3, 7.3, 14.5, 15.6, and 24.0 and infusion rates of 12.5, 15.0, 18.75, 23.75, 30.0, 37.5 and 50 mg/m$^2$/h, respectively.

FIG. 3A time course of PSA [ng/ml] in Patient #27, and FIG. 3B is a time course of CEA [ug/l] and Ca19-9 [U/ml] in Patient #30.

DETAILED DESCRIPTION OF THE INVENTION

Figure 1A:
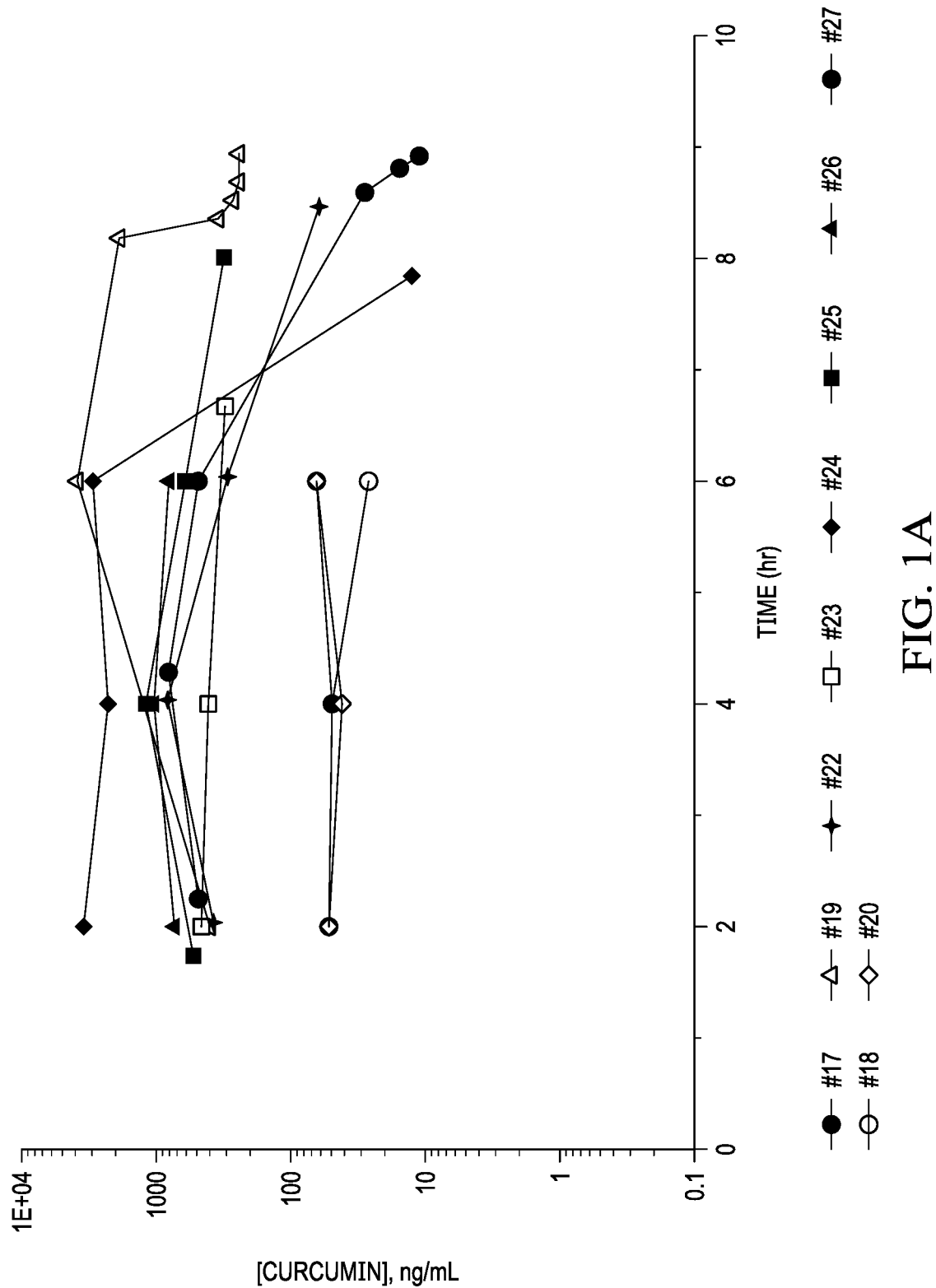
FIGS. 1A and 1B show the results for curcumin plasma concentration curves during infusion with Curcumin. Plasma levels of curcumin are shown for individual subjects. Time (h) represents the actual sampling times. Time "0" represents the start of infusion.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The invention provides compositions and dosing regimens useful for treatment or prevention of cancers of any of a wide variety of types, including both solid tumors and non-solid tumors such as leukemia and lymphoma. It has been found that the dosing regimen of the present invention can be used to treat either malignant or benign cancers. In certain examples, the dosing regimen of the present invention may be varied within certain parameters. Generally, the dosing regimen for treating a proliferative disorder comprises administering a therapeutically effective amount of an intravenous liposomal curcumin or analog thereof (curcuminoids) that are isolated from the turmeric plant or synthesized to a high level of purity, to a human subject in need thereof in accordance with a dosing regimen comprising: at least one treatment cycle administering the therapeutically effective amount of the intravenous liposomal curcumin once per week of at least 100 mg/m$^2$ over 8 hours. The treatment cycle can be followed by a rest period of 1 week during which no the intravenous liposomal curcumin or analog thereof is administered. Often, and depending on the monitoring of the effect of the formulation, the treatment cycle can be repeated for, e.g., 2, 3, 4, 5, 6, 7, 8, 9, or 10, 11, or 12, consecutive weeks. The dosage of the intravenous liposomal curcumin or analog thereof that is administered may be at a dose of, e.g., 150, 200, 250, 300, 350, 400, 450, or 460 mg/m$^2$. The dosage of the intravenous liposomal curcumin or analog thereof that is administered may be at a dose of, e.g., 100 to 460 mg/m$^2$, over 2 to 6 hours. The dosage of the intravenous liposomal curcumin or analog thereof that is administered may be at a dose of, e.g., 200 to 500 mg/m$^2$, over 2 to 4 hours. The dosage of the intravenous liposomal curcumin or analog thereof that is administered may be at a dose of intravenous liposomal curcumin or analog thereof is administered for, e.g., 2, 3, 4, 5, 6, or 7 hours, or fractions thereof (e.g., +/−15, 20, 30, 45, or 50 minutes). The dosage of the intravenous liposomal curcumin or analog thereof that is administered may be at a dose of at least 300 mg/m$^2$ over, e.g., 2, 3, 4, 5, 6, 7, or 8 hours. In certain embodiments the dosing is 300mg, 400mg, 460mg, 500mg, or 600mg. In certain embodiments, the infusion time is 6 hours or less, 4 hours or less, or 2 hours or less. In certain embodiments, the frequency of infusion is 1x per 6 days, 1x per 5 days, or 1x per 4 days.

Non-limiting examples of target proliferative disease for treatment using the present invention include carcinomas, sarcomas, myelomas, gliomas, lymphomas, and leukemias can all be treated using the present invention, including those cancers which have a mixed type. Specific types of cancer that can also be treated include, but are not limited to: adenocarcinoma of the breast or prostate; all forms of bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell, and transitional cell), histiocytic disorders; leukemia (e.g., B-cell, mixed-cell, null-cell, T-cell, T-cell chronic, HTLV-II-associated, lyphocytic acute, lymphocytic chronic, mast-cell, and myeloid); histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; Ewing's sarcoma; synovioma; adenofibroma; adenolymphoma; carcinosarcoma; chordoma; craniopharyngioma; dysgermiinoma; hamartoma; mesenchymoma; mesonephroma; myosarcoma; ameloblastoma; cementoma; odontoma; teratoma; thymoma; trophoblastic tumor; adenocarcinoma; adenoma; cholangioma; cholesteatoma; cylindroma; cystadenocarcinoma; cystadenoma; granulosa cell tumor; gynandroblastoma; hepatoma; hidradenoma; islet cell tumor; leydig cell tumor; papilloma; sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; multiple myeloma, neurilemmoma; neuroblastoma;

neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma (e.g., Ewing's, experimental, Kaposi's, and mast-cell); neoplasms (e.g., bone, breast, digestive system, colorectal, liver, pancreatic, pituitary, testicular, orbital, head and neck, central nervous system, acoustic, pelvic, respiratory tract, and urogenital); neurofibromatosis, and cervical dysplasia), and the like.

The dosing regimens of the present invention are also useful for the treatment or prevention of cancer in all mammalian subjects, e.g., human patients. As used herein, a patient is a human patient. Also as used herein, treatment means any amelioration of the cancer.

As used herein, "dosing regimen" refers to the specific dosages, timing of dosages, repeat times for dosages, and the use of compositions or medicaments to treat patients and other mammalian subjects having cancer in order to at least ameliorate the symptoms of cancer or to halt, inhibit or reverse the progress of the disease. The skilled artisan will recognize that the same compositions and dosing regimen(s) may have different effects on different patients, and even different effects on the same patient at different times. As used herein, "prevention" refers to treating patients prophylactically to prevent or inhibit onset of cancer in patients or mammalian subjects who have a susceptibility to developing the disease.

As used herein, "curcumin" and "curcumin analogs" refer to those compounds that due to their structural similarity to curcumin, exhibit anti-proliferative or pro-apoptotic effects on cancer cells similar to that of curcumin. Curcumin is a natural product found in the plant turmeric, with the chemical name diferuloylmethane. The molecular formula is $C_{21}H_{20}O_6$ with a molar mass of 368.38 g/mol. Curcumin acts as an anti-cancer-therapeutic by promoting death pathways and limiting survival pathways in tumor cells. Despite its activity against mature cancer cells and cancer stem cells, curcumin is known to have little toxicity against normal cells, even with long-term. This may be because the uptake of curcumin is much greater in cancer cells than in normal cells. Curcumin also has different effects on cancer stem cells and normal stem cells. Through its anti-inflammatory effects, curcumin changes the microenvironment around the cancer cell to one that is adverse to proliferation of cancer stem cells but conducive to normal stem cells. In fact, curcumin has been shown, in multiple studies, to have stimulatory and protective effects on normal stem cell function. A limiting factor for the therapeutic use of curcumin is its poor water solubility and corresponding poor bioavailability after oral intake. To overcome the pharmacokinetic and bioavailability limitations of oral administration a liposomal formulation of curcumin has been developed for intravenous administration and represents a promising drug delivery system.

Curcumin analogs which may have anti-cancer effects similar to curcumin include Ar-tumerone, methylcurcumin, demethoxy curcumin, bisdemethoxycurcumin, sodium curcuminate, dibenzoylmethane, acetylcurcumin, feruloyl methane, tetrahydrocurcumin, 1,7-bis(4-hydroxy-3-methoxyphenyl)-1,6-heptadiene-3,5-dione (curcuminI), 1,7-bis(piperonyl)-1,6-heptadiene-3,5-dione(piperonyl curcumin) 1,7-bis(2-hydroxy naphthyl)-1,6-heptadiene-2,5-dione(2-hydroxyl naphthyl curcumin), 1,1-bis(phenyl)-1,3,8,10-undecatetraene-5,7-dione (cinnamyl curcumin) and the like (Araujo and Leon, 2001; Lin et al., 2001; John et al., 2002; see also Ishida et al., 2002). Curcumin analogues may also include isomers of curcumin, such as the (Z,E) and (Z,Z) isomers of curcumin. In a related embodiment, curcumin metabolites, which have anti-cancer effects similar to curcumin can also be used in the present invention. Known curcumin metabolites include glucoronides of tetrahydrocurcumin and hexahydrocurcumin, and dihydroferulic acid. In certain embodiments, curcumin analogues or metabolites can be formulated as metal chelates, especially copper chelates. Other appropriate derivatives of curcumin, curcumin analogues and curcumin metabolites appropriate for use in the present invention will be apparent to one of skill in the art.

As used herein, the term "lipid" refers to lipids, for example, phospholipids, with the optional addition therewith of a sterol, especially cholesterol. The lipids can be provided alone or in combination with other lipids, can be saturated and unsaturated, branched or unbranched, can be in the form of a lipid tri-glycerol molecule. Non-limiting examples of phospholipids for use with the present invention include but are not limited to, e.g., 1,2-Dimyristoyl-sn-glycero-3-phosphorylcholine (DMPC), 1,2-Dimyristoyl-sn-glycero-3-phosphorylglycerol (DMPG), DMPC/DMPG, 1-myristoyl-2-hydroxy-sn-glycero-3-phospho-(1'-rac-glycerol) (LysoPG), 1-myristoyl-2-hydroxy-sn-glycero-3-phospho-(1'-rac-glycerol) (LysoPG), 1-myristoyl-2-hydroxy-sn-glycero-3-phosphocholine (LysoPC), lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. Other non-limiting exemplary lipids for use with the present invention include, e.g., phosphatidylcholine, a phosphatidylethanolamine, a phosphatidylserine, a phosphatidylglycrol, a cardiolipin, a phosphatidylinositol or a precursor thereof in lipid, liposome, or lyso form. Non-limiting examples of lipids include lysophosphatidylglycerols for use with the present invention include lysophosphatidylcholines, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. Asymmetric phosphatidylcholines are referred to as 1-acyl, 2-acyl-sn-glycero-3-phosphocholines, wherein the acyl groups are different from each other. Symmetric phosphatidylcholines are referred to as 1,2-diacyl-sn-glycero-3-phosphocholines. As used herein, the abbreviation "PC" refers to phosphatidylcholine. The phosphatidylcholine 1,2-dimyristoyl-sn-glycero-3-phosphocholine is abbreviated herein as "DMPC." The phosphatidylcholine 1,2-dioleoyl-sn-glycero-3-phosphocholine is abbreviated herein as "DOPC." The phosphatidylcholine 1,2-dipalmitoyl-sn-glycero-3-phosphocholine is abbreviated herein as "DPPC." The single fatty acid chain version of these short or long chain fatty acids are referred to as the "lyso" forms when only a single fatty acid chain is attached to the glyceryl backbone. Following the guidance of the present invention, other lipids can be identified that have the claimed function as taught herein without undue experimentation. In one aspect, the liposomal curcumin or curcuminoids (liposomal curcumin), comprises a curcumin/curcuminoid:liposome complex, wherein the curcumin comprises between 2 to 9 weight percent of the curcumin/curcuminoid:liposome complex, wherein the curcumin is at least one of natural or synthetic curcumin and wherein the curcumin/curcuminoid:liposome complex has a ratio of curcumin to lipid (weight to weight) of 1:7.5 to 1:10, wherein the lipid combination is selected from: DMPC; DMPC:Chol 9:1; DMPC:DMPG 9:1; DMPC:Chol:DMPG 8:1:1; DPPC:DMPG 9:1; DPPC:Chol:DMPG 8:1:1; DMPC:DSPE-PEG-2000 95:5; DMPC:Chol:DSPE-PEG-2000 90:10:05; DMPC/DMPG 7:3; DPPC/DMPG 7:3; DPPC/DMPG 9:1.

The term "liposome" refers to a capsule wherein the wall or membrane thereof is formed of lipids, especially phospholipid, with the optional addition therewith of a sterol, especially cholesterol. In one specific non-limiting example the liposomes are empty liposomes and can be formulated from a single type of phospholipid or combinations of phospholipids. The empty liposomes can further include one or more surface modifications, such as proteins, carbohydrates, glycolipids or glycoproteins, and even nucleic acids such as aptamers, thio-modified nucleic acids, protein nucleic acid mimics, protein mimics, stealthing agents, etc. Non-limiting examples of empty liposomes for use with the present invention include but are not limited to, e.g., 1,2-Dimyristoyl-sn-glycero-3-phosphorylcholine (DMPC), 1,2-Dimyristoyl-sn-glycero-3-phosphorylglycerol (DMPG), DMPC/DMPG, 1-myristoyl-2-hydroxy-sn-glycero-3-phospho-(1'-rac-glycerol) (LysoPG), and 1-myristoyl-2-hydroxy-sn-glycero-3-phospho-(1'-rac-glycerol) (LysoPG). In one embodiment, the liposome is a liposome or a liposome precursor comprising, e.g., a LysoPG, a myristoyl monoglyceride, and a myristic acid. In one specific, non-limiting example the composition also comprises an active agent in or about the liposome and the composition has a ratio of phospholipids to active agent of 3:1, 1:1, 0.3:1, and 0.1:1.

As used herein, the term "treatment" refers to the treatment of the conditions mentioned herein, particularly in a patient who demonstrates symptoms of the disease or disorder.

As used herein, the term "treatment" or "treating" refers to any administration of a compound of the present invention and includes (i) inhibiting the disease in an animal that is experiencing or displaying the pathology or symptomatology of the diseased (i.e., arresting further development of the pathology and/or symptomatology); or (ii) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

As used herein, the terms "effective amount" or "therapeutically effective amount" described herein means the amount of the subject compound that will elicit the biological or medical response of a tissue, system, animal or human that is being sought by the researcher, veterinarian, medical doctor or other clinician.

As used herein, the terms "administration of" or "administering a" compound as used herein should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories. Methods of administration that can be employed in the present invention also include intraarterial, intramuscular, subcutaneous, intra-tissue, intranasal, intradermal, instillation, intracerebral, intrarectal, intravaginal, intraperitoneal, intratumoral, juxtaposition of tumor and administration directly to the lesion.

As used herein the term "intravenous administration" includes injection and other modes of intravenous administration.

As used herein, the term "pharmaceutically acceptable" as used herein to describe a carrier, diluent or excipient must be compatible with the other ingredients of the formulation and not deleterious to the recipient thereof.

As used herein, the term "pharmaceutically acceptable" or "pharmacologically acceptable" refer to molecular entities and compositions that typically do not produce an adverse, allergic or other untoward reaction when administered to an animal or a human, as appropriate. As used herein, the term "pharmaceutically acceptable carrier" refers to any and all solvents, diluents, dispersion media, coatings, preservatives, isotonic and absorption delaying agents, buffers, excipients, binders, lubricants, gels, detergents, surfactants and the like, that may be used as a media for a pharmaceutically acceptable substance.

The pharmaceutical compositions of the present invention comprising curcumin or a curcumin analogue and a colloidal drug delivery carrier such as a liposome, or empty liposomes, or a combination thereof that are prepared according to standard techniques. They can further comprise a pharmaceutically acceptable carrier. Generally, a pharmaceutical carrier such as normal saline will be employed. Other suitable carriers include water, buffered water, isotonic aqueous solutions, 0.4% saline, 0.3% aqueous glycine and the like, including glycoproteins for enhanced stability, such as albumin, lipoprotein and globulin. These compositions can be sterilized by conventional sterilization techniques that are well-known to those of skill in the art. Sufficiently small liposomes, for example, can be sterilized using sterile filtration techniques. Formulation characteristics that can be modified include, for example, the pH and the osmolality. For example, it may be desired to achieve a formulation that has a pH and osmolality similar to that of human blood or tissues to facilitate the formulation's effectiveness when administered, e.g., intravenously. Alternatively, to promote the effectiveness of the disclosed compositions when administered via other administration routes, alternative characteristics may be modified.

The formation and use of liposomes is generally known to those of skill in the art, as described in, e.g. Liposome Technology, Vols. 1, 2 and 3, Gregory Gregoriadis, ed., CRC Press, Inc; Liposomes: Rational Design, Andrew S. Janoff, ed., Marcel Dekker, Inc.; Medical Applications of Liposomes, D. D. Lasic and D. Papahadjopoulos, eds., Elsevier Press; Bioconjugate Techniques, by Greg T. Hermanson, Academic Press; and Pharmaceutical Manufacturing of Liposomes, by Francis J. Martin, in Specialized Drug Delivery Systems (Praveen Tyle, Ed.), Marcel Dekker, Inc. Forming liposomes typically involves first suspending phospholipids in an organic solvent and then evaporating to dryness until a dry lipid cake or film is formed. An appropriate amount of aqueous medium is added and the lipids spontaneously form multilamellar concentric bilayer vesicles (also known as multilamellar vesicles (MLVs). These MLVs can then be mechanically dispersed. MLVs generally have diameters of from 25 nanometers to 4 micrometers. Sonication of MLVs results in the formation of small unilamellar vesicles (SUVs) with diameters in the range of 200 to 500 angstroms, containing an aqueous solution in the core. SUVs are smaller than MLVs and unilamellar.

The present invention demonstrates, for the first time, the safety and tolerability of liposomal curcumin administered as an intravenous infusion over 8 hours or 6 hours in patients with locally advanced or metastatic cancer for whom no anti-tumor therapy of proven benefit was available at study enrolment. It was also possible to evaluate the $P_k$ of curcumin and THC during and following a first infusion, and to evaluate antitumor activity of liposomal curcumin according to RECIST V1.1 (proportion of patients reaching complete response (CR)/(partial response (PR)/stable disease (SD) after 8 weeks).

Patients. 32 patients with metastatic cancer were treated with liposomal curcumin infusions at doses between 100 and 300 mg/m$^2$ over either 24, 8 or 6 hours. Median age of patients at study entry was 62.7 years (range 42.6-84.5 years) and the majority were male (71.9%). The primary diagnoses of patients were uveal melanoma-1; squamous carcinoma, unknown primary-1; squamous carcinoma of head and neck-2; carcinoma of the parotid gland-1; breast carcinoma-1; lung carcinoma-1; squamous carcinoma, esophagus-2; adenocarcinoma, esophagus or stomach-5; hepatocellular carcinoma-2; cholangiocarcinoma-3; adencarcinoma of pancreas-3; adenocarcinoma, small bowel-1; colon carcinoma-1; anal epidermoid carcinoma-2; urothelial carcinoma-3; uterine carcinoma-1; prostate carcinoma-2. Patients were heavily pretreated with a median of 5 previous cancer treatments (range 2-10) (Table 1). Patients received between 1 and 11 infusions of liposomal curcumin and the median treatment duration was 38.5 days (range 1-82 days) (Table 1). 17 patients (53.1%) received at least 5 infusions of the study medication whereas 8 patients (25.0%) received all planned 8 infusions. Treatment was stopped after disease progression (23 patients), deterioration of general medical condition (6 patients), early withdrawal (2 patients) or study interruption (1 patient). While for most patients the reason for study end was death, only 10 patients died within 4 weeks after the last study treatment.

TABLE 1

Patient characteristics.

| | | other | DL 1 | DL 2 | DL 3 | DL 4 | DL 5 | DL 6 | DL 6a | all |
|---|---|---|---|---|---|---|---|---|---|---|
| | | | | | Curcumin DLs | | | | | |
| | [mg/m$^2$] | 120 | 100 | 120 | 150 | 190 | 240 | 300 | 300 | — |
| | | | | | Duration of infusion | | | | | |
| | [hours] | 24 | 8 | 8 | 8 | 8 | 8 | 8 | 6 | — |
| | | | | | Number of patients | | | | | |
| | n | 1 | 4 | 7 | 4 | 3 | 3 | 4 | 6 | 32 |
| | | | | | Gender | | | | | |
| male | n (%) | 1 | 4 (100) | 5 (71) | 2 (50) | 1 (33) | 2 (67) | 4 (100) | 4 (67) | 23 (72) |
| female | n (%) | 0 | 0 (0) | 2 (29) | 2 (50) | 2 (67) | 1 (33) | 0 (0) | 2 (33) | 9 (28) |
| | | | | | Age [years] | | | | | |
| | Median | 65.2 | 63.7 | 58.2 | 72.8 | 61.8 | 60.6 | 67.0 | 60.3 | 62.7 |
| | Range | 65.2 | 50.4-68.9 | 42.6-69.8 | 66.7-84.5 | 48.2-62.2 | 58.6-69.4 | 57.0-76.9 | 48.0-72.9 | 42.6-84.5 |
| | | | | | Number of previous treatment regimes | | | | | |
| 2 | n | 1 | — | — | — | — | — | — | — | 1 |
| 3 | n | — | — | 1 | 1 | 1 | — | — | — | 3 |
| 4 | n | — | 2 | 1 | 4 | — | 1 | 1 | 1 | 10 |
| 5 | n | — | 1 | 5 | 5 | — | — | 2 | 1 | 14 |
| 6 | n | — | 1 | 2 | — | 1 | — | — | — | 4 |
| 7 | n | — | — | 1 | — | — | — | 1 | 1 | 3 |
| 8 | n | — | — | — | — | 1 | 1 | — | 2 | 4 |

TABLE 1-continued

| Patient characteristics. | | | | | | | | | | |
|---|---|---|---|---|---|---|---|---|---|---|
| | | other | DL 1 | DL 2 | DL 3 | DL 4 | DL 5 | DL 6 | DL 6a | all |
| 9 | n | — | — | — | — | — | — | — | 1 | 1 |
| 10 | n | — | — | — | — | — | 1 | — | — | 1 |
| ECOG Score | | | | | | | | | | |
| 0 | n | 1 | — | 2 | 1 | 1 | 1 | — | 3 | 9 |
| 1 | n | — | 4 | 3 | 3 | 1 | 1 | 2 | 2 | 16 |
| 2 | n | — | — | 2 | — | 1 | 1 | 2 | 1 | 7 |
| Mean Treatment duration | | | | | | | | | | |
| | [days] | 15 | 31 | 33.3 | 27.5 | 38.3 | 38.3 | 26.8 | 54.2 | 35.8 |

Adverse Events (AEs). A total of 143 AEs were experienced by 30 patients (93.8%). Out of these AEs only 34 AEs (in 14 patients) were considered definitely, probably or possibly related to the study treatment while most others were considered related to underlying disease. Surprisingly, infusions of liposomal curcumin over 8 hours at DL 1-6 (100-300 mg/m$^2$) were generally well tolerated at DL 6a (300 mg/m$^2$ over 6 hours) the number of observed hematological AEs considered related to the study drug increased notably (Table 2).

hyponatremia in patient #3). Hemolysis and anemia were observed in DL 6a and resulted in stop of dose escalation (see DLT). Patient #3, with a history of liver cirrhosis, ascites, generalized edema and a pre-existing hyponatremia developed a Grade 3 hyponatremia with a decrease in serum sodium from 133 mmol/L before the first infusion to a low of 126 mmol/L before the sixth infusion.

DLT and recommended Phase 2 Dose. Six patients were included in DL 6a. One patient (#28) displayed definite signs of hemolysis. During cycle 2 the patient's hemoglobin (Hb)

TABLE 2

Adverse Events with definite or probable causal relationship to study treatment.

| DL | Patient | AE (Preferred term) | Timing | Grade | SAE | Relationship | Outcome |
|---|---|---|---|---|---|---|---|
| 1 | 002 | Red blood cell abnormality | cycle 1 | n.a. | no | definite | recovered |
| | 003 | Platelet count decreased | cycle 1 | 2 | no | probable | recovered with sequelae |
| | | Platelet count decreased | cycle 2 | 2 | no | probable | recovered with sequelae |
| | 004 | Pyrexia | cycle 1 | 1 | no | probable | recovered |
| | | Productive cough | cycle 1 | 1 | no | probable | recovered |
| | | Pyrexia | cycle 2 | 1 | no | probable | recovered |
| | | Chills | cycle 5 | 2 | no | probable | recovered |
| | | Pyrexia | cycle 5 | 1 | no | probable | recovered |
| 5 | 023 | Hypertrichosis | cycle 4 | 1 | no | probable | recovered |
| 6a | 028 | Anemia | cycle 3 | 2 | no | probable | ongoing after final examination |
| | 028 | Haemolysis | cycle 4 | 3 | no | definite | recovered with sequelae |
| | 029 | Anemia | cycle 4 | 3 | no | definite | ongoing after final examination |
| | 030 | Infusion related reaction | cycle 7 | 2 | no | probable | recovered |
| | 031 | Face edema | cycle 1 | 2 | yes | probable | recovered |
| | 032 | Anemia | cycle 1 | 3 | yes | probable | recovered |
| | 032 | Anemia | cycle 2 | 2 | no | definite | recovered |

Of the 40 reported SAEs in 23 patients (71.9%) 2 were related to study treatment (patient #31 edema face, patient #32 anemia). Both patients were treated in DL 6a. Echinocytes were observed in one patient (#2) in DL 1 (100 mg/m$^2$). Cardiac, pulmonary, hepatic or renal toxicity related to the study medication was not observed and only 3 Grade 1 gastrointestinal AEs possibly related to study medication were observed.

A total of 4 AEs were rated Grade 3 by the investigator (anemia in patients #29, #32, hemolysis in patient #28, decreased from 11.5 g/dl (start of infusion) to 9.5 g/dl (end of infusion-EOI) to 9.1 g/dl (3 h after EOI), haptoglobin decreased slightly. During cycle 4 Hb decreased from 8 g/dl (start) to 6.4 g/dl (EOI) to 5.5 g/dl (2.5 h after EOI), haptoglobin decreased considerably from 130 mg/dl (start) to 89 mg/dl (EOI) to 15 mg/dl (2.5 h after EOI) to <10 mg/dl (15 h after EOI) (normal range 30-200 mg/dl). In both treatment cycles the patient also showed elevated bilirubin, reticulocytes (%) and LDH. Hemolysis related to study treatment was documented as adverse event for cycle 4.

Between cycles 1 and 2 the patient suffered from port-a-cath infection (SAE) and received erythrocyte transfusion. Between cycles 3 and 4 the patient had anemia grade 2, probably related to a concurrent infection and received another erythrocyte transfusion. Blood smears showed no fragmentocytes or echinocytes.

Clinically significant drop of Hb (>2 g/dl) related to infusion of liposomal curcumin was only observed in three other patients (#29, #32, #33), however the presence hemolysis was not definite in these patients since haptoglobin and MCV did not change. Blood smears showed no fragmentocytes or echinocytes. In addition, the patients showed no signs of bleeding. In Patient #32 Hb decreased to 5.5 after cycle 2 and the experienced anemia was documented as SAE with definite relationship to study treatment (SUSAR). Patients #30 and #31 did not experience clinically significant drops in Hb.

One patient (#31) developed a facial edema (G2) during the night after the first infusion, which was treated with dexamethasone and dibondrin and required a prolongation of hospitalization for further observation. The patient recovered within one day and study treatment was continued without further occurrence of facial edema.

Figure 1B:
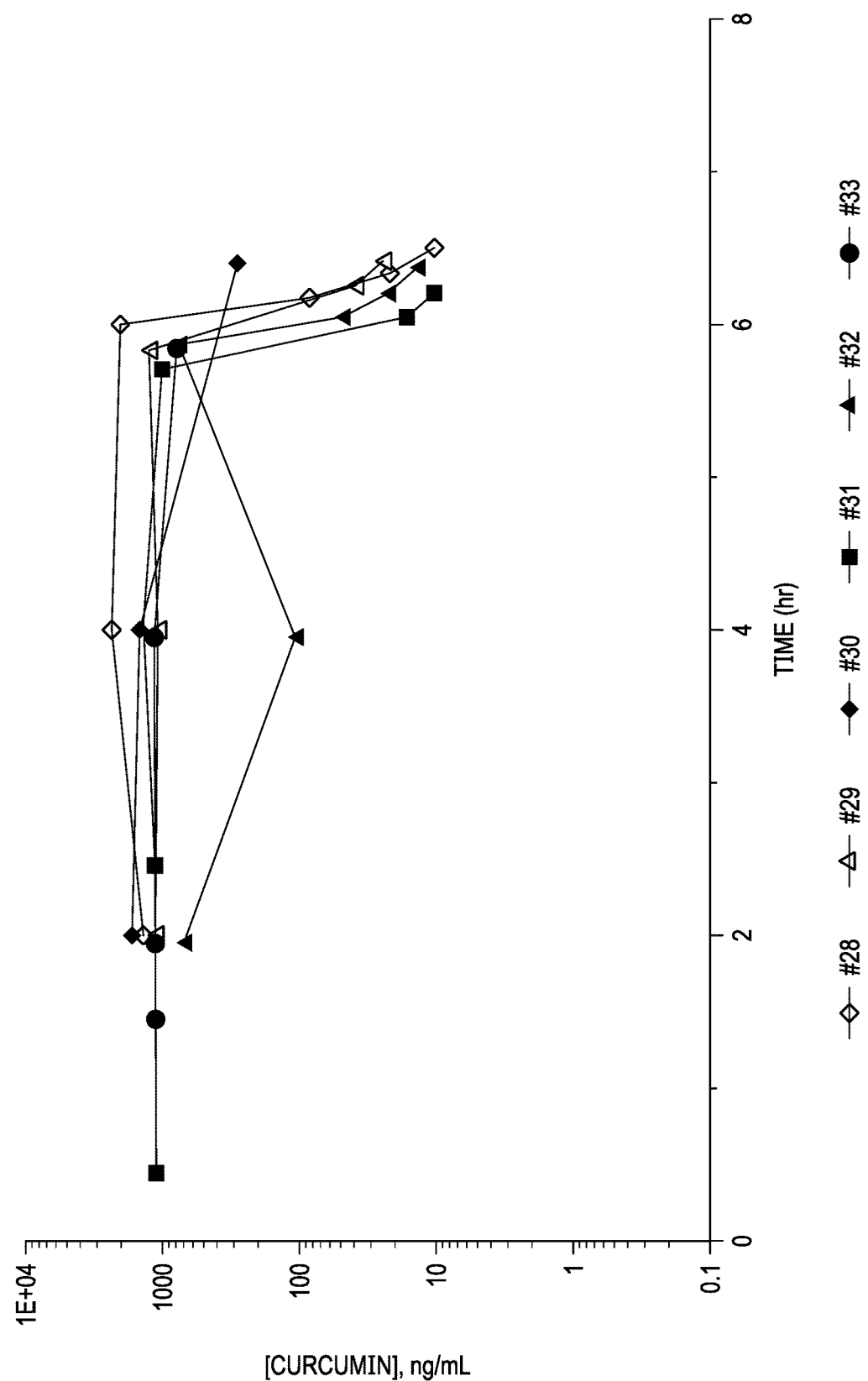
Figure 2A:
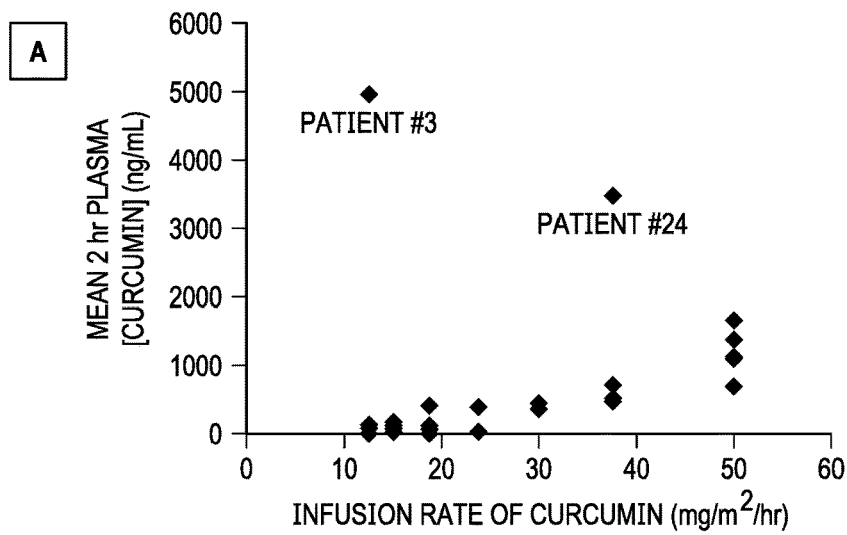
FIGS. 2A to 2C show plasma levels of Curcumin at 2 h during infusion compared to the infusion rate.
Figure 2B:
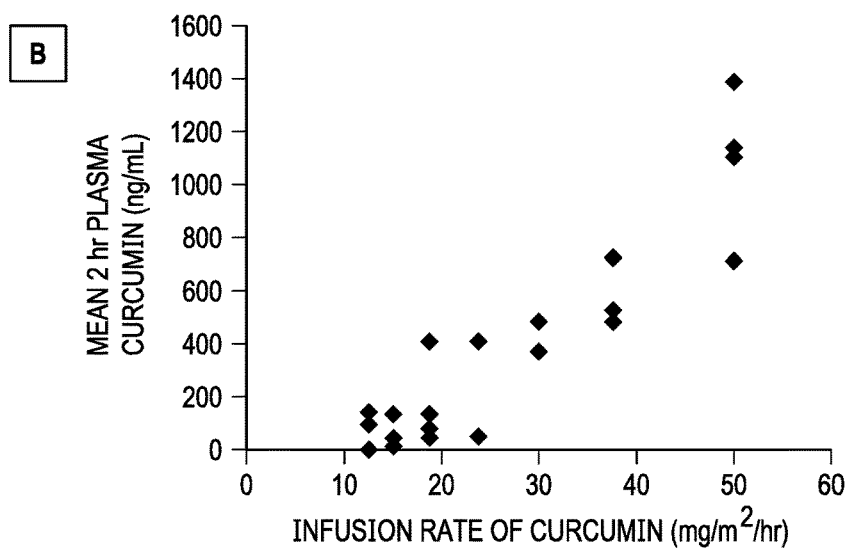
Figure 2C:
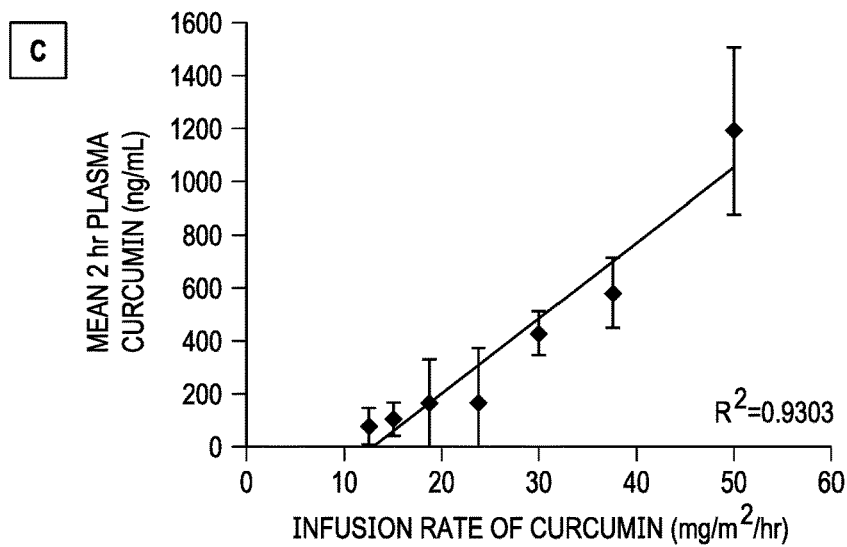

Pharmacokinetics of Curcumin and THC. Blood samples for PK evaluation of curcumin and THC were collected and the plasma isolated from all patients who received the first infusion of liposomal curcumin over 8 or 6 hours. Patient #21 was excluded from the PK analysis because the infusion was interrupted for 1.5 h. For patients treated at dose levels DL 1-DL 3 (100 to 150 mg/m$^2$) who had only one blood collection during infusion (before amendment 3), the PK parameters were not evaluated since most of the plasma samples were below the limit of quantification (BLOQ) for curcumin and THC. PK parameters for patients #17-#33 are presented in Table 3. Individual curcumin plasma concentrations-time curves for those patients are depicted in FIGS. 1A and 1B. The mean $T_{max}$ for curcumin was achieved during infusion, and ranged from 3.6-4.0 hours across a dose range of 190-300 mg/m$^2$ and 4.2 hours for the 6 h infusion. While steady-state levels of curcumin were achieved for most of the patients, patient #19 did not achieve steady-state levels of curcumin with plasma levels increasing between 2 and 6 hours of infusion from 413.81 to 3885.14 ng/mL (FIG. 1), resulting in considerably higher $AUC_{0-Tlast}$ value compared to other patients in the 190 mg/m$^2$ dose group (Table 3). In general, however, $AUC_{0-Tlast}$ values increased with increasing infusion doses of curcumin. At the EOI plasma levels rapidly decreased to BLOQ within 10 min. In order to compare the plasma levels of curcumin achieved after different infusion doses and infusion times and to include as many data points as possible, the plasma levels of curcumin in patients following 2 hours of infusion were compared to the infusion rates. FIG. 2A depicts the relationship between infusion rate and curcumin plasma levels of patients at 2 h during infusion with dose levels of 100, 120, 150, 190, 240 and 300 mg/m$^2$ over 8 hours and 300 mg/m$^2$ over 6 hours corresponding to infusion rates of 12.5, 15, 18.75, 23.75, 37.5 and 50 mg/m$^2$/h, respectively. It is apparent that patients #3 and #24 had very high 2 h plasma concentrations compared to all other patients. In order to understand the relationship between infusion rate and plasma concentrations for the remaining patients the data for patients #3 and #24 were removed (FIG. 2B). Mean plasma concentrations of curcumin for the remaining 29 patients displayed an apparent linear dependence with infusion rate ($R^2$=0.9303). However, infusion rate normalized mean plasma concentrations of curcumin ranged between 7.0-9.3 up to an infusion rate of 23.75 mg/m$^2$/h and ranged between 14.5-24.0 between infusion rates of 30-50 mg/m$^2$/h, suggesting greater than dose proportional increases of plasma curcumin concentrations at higher infusion rates (FIG. 2C).

TABLE 3

PK parameter for Curcumin

| Patient | $C_{max}$ [ng/ml] | $T_{max}$ [h] | $AUC_{0-Tlast}$ [ng·h/ml] | $C_{last}$ [ng/mL] | $T_{last}$ [h] |
|---|---|---|---|---|---|
| DL 3: 150 mg/m$^2$, 8 h infusion | | | | | |
| 17 | 66.1 | 6.0 | 270 | 66.1 | 6.0 |
| DL 4: 190 mg/m$^2$, 8 h infusion | | | | | |
| 18 | 54.7 | 2.0 | 231 | 26.4 | 6.0 |
| 19a | 3885.1 | 6.0 | 13752 | 251.2 | 8.8 |
| 20 | 64.1 | 6.0 | 254 | 64.1 | 6.0 |
| Mean | 59.4 | 4.0 | 243 | 45.3 | 6.0 |
| SD | 6.7 | 2.8 | 16 | 26.7 | 0 |
| SE | 4.7 | 2.0 | 12 | 18.8 | 0 |
| % CV | 11 | 71 | 7 | 59 | 0 |
| DL 5: 240 mg/m$^2$, 8 h infusion | | | | | |
| 22 | 824.2 | 4.0 | 3077 | 61.9 | 8.5 |
| 23 | 469.4 | 2.0 | 2325 | 310.4 | 6.7 |
| Mean | 646.8 | 3.0 | 2701 | 186.2 | 7.6 |
| SD | 250.9 | 1.4 | 532 | 175.7 | 1.3 |
| SE | 171.4 | 1.0 | 376 | 124.3 | 0.9 |
| % CV | 39 | 48 | 20 | 94 | 17 |
| DL 6: 300 mg/m$^2$, 8 h infusion | | | | | |
| 24 | 3484.4 | 2.0 | 17351 | 12.9 | 7.8 |
| 25 | 1212.3 | 4.0 | 5174 | 319.1 | 8.0 |
| 26 | 1051.4 | 4.0 | 4374 | 807.1 | 6.0 |
| 27 | 815.8 | 4.3 | 3674 | 11.3 | 8.9 |
| Mean | 1641 | 3.6 | 7643 | 287.6 | 7.7 |
| SD | 1239.7 | 1.1 | 6501 | 375.4 | 1.2 |
| SE | 715.7 | 0.6 | 3753 | 216.7 | 0.7 |
| % CV | 76 | 30 | 85 | 131 | 16 |
| DL 6a: 300 mg/m$^2$, 6 h infusion | | | | | |
| 28 | 2351.2 | 4.0 | 9701 | 10.4 | 6.5 |
| 29 | 1261.8 | 5.8 | 5780 | 24.9 | 6.4 |
| 30 | 1672.7 | 2.0 | 6915 | 286.2 | 6.4 |
| 31 | 1367.6 | 4.0 | 6669 | 10.6 | 6.2 |
| 32 | 767.2 | 5.9 | 2448 | 13.8 | 6.4 |
| 33 | 1147.7 | 4.0 | 5168 | 790.2 | 5.8 |
| Mean | 1428 | 4.3 | 6113 | 189.4 | 6.3 |
| SD | 540.1 | 1.4 | 2378 | 313.8 | 0.2 |
| SE | 220.5 | 0.6 | 971 | 128.1 | 0.1 |
| % CV | 38 | 34 | 39 | 166 | 4 | aData for patient #19 were not included in the calculation of the mean, SD, SE and % CV.

The pattern of plasma concentrations for THC was similar to that for curcumin, but the plasma levels of THC expressed as percentage of the $AUC_{0-TLast}$ of THC to curcumin were considerably lower ranging from 2.1%-21.8% (mean of 8.5%) of the plasma levels of curcumin at 2-4 hours across individual patients during infusion. The PK parameters for THC are shown in Table 4.

Table 4 shows the pharmokinetic parameters for tetrahydrocurcumin.

| Patient | $C_{max}$ [ng/ml] | $T_{max}$ [h] | $AUC_{0-Tlast}$ [ng·h/ml] | $C_{last}$ [ng/mL] | $T_{last}$ [h] | $AUC_{0-Tlast}$ THC/ $AUC_{0-Tlast}$ Curcumin |
|---|---|---|---|---|---|---|
| DL 3: 150 mg/m$^2$, 8 h infusion | | | | | | |
| 17 | 16.1 | 4 | 59 | 10.3 | 6.0 | 0.218 |

-continued

| Patient | $C_{max}$ [ng/ml] | $T_{max}$ [h] | $AUC_{0\text{-}Tlast}$ [ng·h/ml] | $C_{last}$ [ng/mL] | $T_{last}$ [h] | $AUC_{0\text{-}Tlast}$ THC/ $AUC_{0\text{-}Tlast}$ Curcumin |
|---|---|---|---|---|---|---|
| DL 4: 190 mg/m², 8 h infusion | | | | | | |
| 18 | 7.7 | 4.0 | 22 | 7.7 | 4.0 | 0.096 |
| 19* | 396.1 | 8.1 | 1656 | 11.8 | 8.8 | 0.122 |
| 20 | 6.6 | 6.0 | 31 | 6.6 | 6.0 | 0.121 |
| Mean | 7.2 | 5.0 | 27 | 7.2 | 5.0 | 0.109 |
| SD | 0.7 | 1.4 | 6 | 0.7 | 1.4 | 0.018 |
| SE | 0.5 | 1.0 | 4 | 0.5 | 1.0 | 0.012 |
| % CV | 10 | 28 | 23 | 10 | 28 | 16 |
| DL 5: 240 mg/m² 8 h infusion | | | | | | |
| 22 | 24.3 | 2.0 | 102 | 14.3 | 6.0 | 0.033 |
| 23 | 63.3 | 2.0 | 271 | 28.2 | 6.7 | 0.116 |
| Mean | 43.8 | 2.0 | 186 | 21.2 | 6.4 | 0.075 |
| SD | 27.6 | 0 | 119 | 9.9 | 0.5 | 0.059 |
| SE | 19.5 | 0 | 84 | 7.8 | 0.3 | 0.042 |
| % CV | 63 | 0 | 64 | 47 | 7 | 79 |
| DL 6: 300 mg/m², 8 h infusion | | | | | | |
| 24 | 108.3 | 2.0 | 359 | 48.2 | 6.0 | 0.021 |
| 25 | 75.2 | 3.8 | 407 | 28.6 | 7.6 | 0.079 |
| 26 | 75.6 | 2.0 | 426 | 5.3 | 8.5 | 0.097 |
| 27 | 38.5 | 2.3 | 187 | 5.1 | 8.6 | 0.051 |
| Mean | 74.4 | 2.5 | 344 | 21.8 | 7.7 | 0.062 |
| SD | 28.5 | 0.8 | 109 | 20.8 | 1.2 | 0.033 |
| SE | 16.5 | 0.5 | 63 | 12.0 | 0.7 | 0.019 |
| % CV | 38 | 34 | 32 | 95 | 16 | 54 |
| DL 6a: 300 mg/m², 6 h infusion | | | | | | |
| 28 | 110.4 | 2.0 | 497 | 6.9 | 6.8 | 0.051 |
| 29 | 35.1 | 4.0 | 155 | 5.2 | 6.8 | 0.027 |
| 30 | 80.1 | 2.0 | 385 | 5.2 | 7.3 | 0.056 |
| 31 | 67.6 | 2.5 | 332 | 6.0 | 6.0 | 0.050 |
| 32 | 70.7 | 5.9 | 321 | 8.4 | 6.6 | 0.131 |
| 33 | 58.3 | 5.8 | 264 | 5.7 | 6.2 | 0.051 |
| Mean | 70.3 | 3.7 | 326 | 6.2 | 6.6 | 0.061 |
| SD | 24.9 | 1.8 | 115 | 1.2 | 0.5 | 0.036 |
| SE | 10.2 | 0.7 | 47 | 0.5 | 0.2 | 0.015 |
| % CV | 35 | 49 | 35 | 20 | 7 | 59 |

*Data for patient #19 were not included in the calculation of the mean, SD, SE and % CV.

Efficacy. The primary efficacy endpoint was the response rate (complete response/partial response/stable disease/progressive disease) according to RECIST v1.1 after 8 weeks. 23 patients had a tumor response assessment but only 8 patients reached the tumor assessment after 8 weeks of treatment. All of them showed PD. Of 15 patients with tumor assessment between week 4 and 8, 14 showed PD and one (patient #27) showed SD. Five patients experienced a deterioration of their general condition after 1 to 4 drug infusions and treatment was stopped without tumor assessment. 2 Patients withdrew their IC.

Figure 3A:
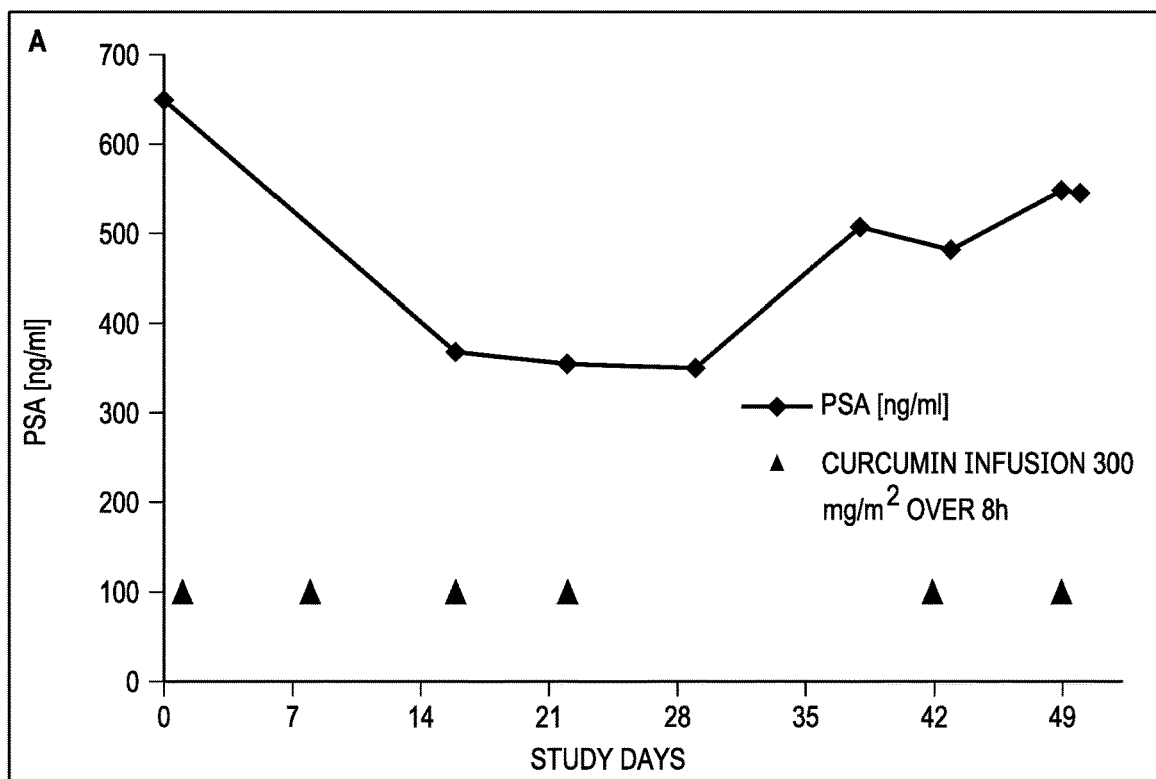
FIGS. 3A and 3B are graphs that show the time course of tumor marker.
Figure 3B:
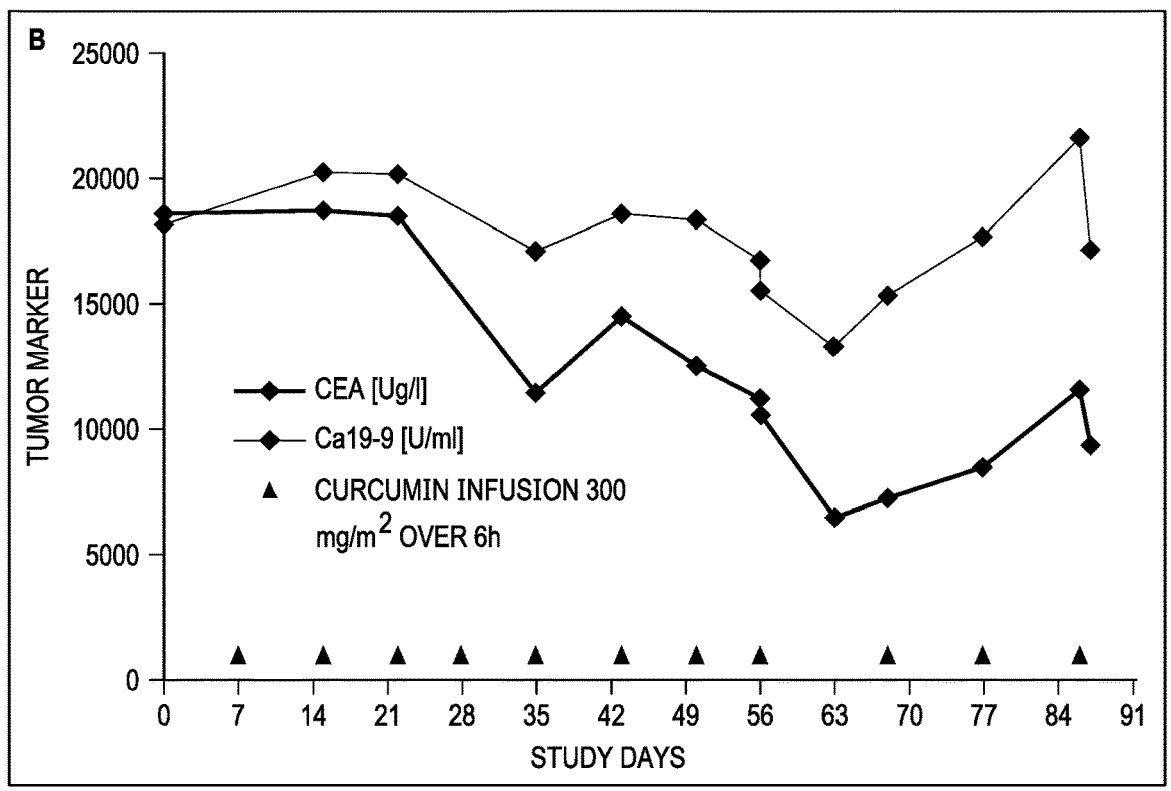

Tumor markers CEA, CA19-9, PSA and CA15-3 were assessed where relevant. In two patients, temporarily a significant reduction of a tumor marker was observed. In patient #27 with prostate cancer and bone and lymph node metastases as well as lymphangiosis of the lung the PSA level was reduced from 649 ng/mL to 355 ng/mL after the 4th infusion. After the $4^{th}$ infusion treatment was interrupted for 3 weeks due to suspected lung infection and the PSA level increased again up to 547 ng/ml (FIG. 3A). A tumor response assessment during the treatment interruption showed SD. The patient received two more curcumin infusions before the study was terminated due to disease progression. During the first four weeks of treatment the investigator reported improved general condition (WHO 2 to WHO 1) and a temporary reduction of LDH was observed from 435 U/L to 202 U/L (normal range 135 -225 U/L). In patient #30 with colon cancer and liver and lung metastases the CEA level was reduced from 18542 µg/l at screening to 6441 µg/l and CA19-9 was reduced from 18105 U/ml at screening to 13238 U/ml after 8 weeks (FIG. 3B) while tumor staging revealed progressive disease. The patient received three more infusions due to clinical benefit and tumor marker response. During this time tumor marker increased again and treatment was stopped after the $11^{th}$ infusion due to reduced general condition. The patient died 13 days after last administration of the study drug. Both patients with tumor marker response were treated at a curcumin dose of 300 mg/m² (patient #27 over 8 hours and patient #30 over 6 hours).

Patients participating in this study generally had advanced cancer, exhausted lines of established anticancer treatments, and were considered ineligible for later-phase clinical studies. Dose escalation of liposomal curcumin was continued until DL 6a (300 mg/² over 6 hours). Infusion of liposomal curcumin over 8 hours at doses between 100 and 300 mg/m² (DL 1-6) were generally well tolerated and the number of reported AEs and SAEs was not unexpected for the heavily pretreated patient population.

At DL 6a (300 mg/m² over 6 hours) the number of observed AEs related to the study drug increased significantly. At this DL a significant decrease of Hb during infusions was observed in 4 of 6 patients. Definite hemolysis, meeting the definition of DLT, was observed in one patient (#28), 3 other patients experienced anemia (#29, #31, #32). While the decrease of Hb observed in these patients was the reason for stopping dose escalation, comparison of changes in Hb in different patients has to be done with caution. These patients had different treatment histories and different degrees of prior bone marrow destruction secondary to different prior chemotherapies and in some patients prior RT. All patients received multiple concomitant medications and some of which might have predisposed the red cells to hemolysis from curcumin. Four of the most common agents that are known to cause hemolysis are levofloxacin, cephalosporins, penicillins and ibuprofen[25-28]. Patient #28 was receiving levofloxacin (tavanic), amoxicillin and ibuprofen (brufen). Patient #32 was receiving a cephalosporin (zinnat), and had been receiving both a penicillin and ibuprofen shortly before starting liposomal curcumin.

It was considered that there might be a threshold for Hb at the start of infusion below which the drop in Hb becomes more considerable. In a heavily pretreated patient population the observed adverse events are expected to increase at higher dose levels. While they can easily be controlled in the hospital this would not be possible in any external setting. Therefore the dose of 300 mg/m² liposomal curcumin monotherapy over 6 h is warranted as recommended starting dose for anti-cancer treatment as the dose was well tolerated. Further, higher doses can be used, e.g., 325, 350, 375, 400, 425, 450, or 475 mg/m² liposomal curcumin. Echinocyte formation was expected especially at higher DLs with AUC and $C_{max}$ comparable to Phase 1a. However, echinocytes were observed in only one patient (#2) at DL 1 (100 mg/m²).

PK analysis showed stable plasma concentration of curcumin and THC during infusion and rapid decline after the end of infusion. At DL 300 mg/m² the mean $C_{max}$ plasma levels of curcumin were similar with 1428-1641 ng/mL for the 6 hrs and 8 hrs infusions. While most patients' plasma levels of curcumin and THC dropped to unquantifiable levels within 10 min after EOI, there was one remarkable exception in patient #19 with a curcumin plasma concentration of 251 ng/ml 45 min after EOI. $C_{max}$ and AUC of curcumin in this patient were also remarkably high and comparable to values observed in patient #24. Interestingly, high curcumin plasma concentrations in patients #3, #19 and #24 were not connected to adverse events or reduction of Hb during infusion comparable to those reported for patients of DL 6a.

In the remaining 29 patients an apparent linear increase of plasma concentrations with infusion rate was observed. However, for a four-fold change in infusion rate (12.5 mg/m²/h to 50 mg/m²/h), there was a 24.0-fold change in the mean 2 h plasma levels of curcumin during infusion, suggesting that with increasing dose, there were deviations from dose proportionality. This is even more apparent if one compares the $C_{max}$ and $AUC_{0-Tlast}$ values for doses of curcumin ranging from 190-300 mg/m². Thus, at higher infusion rates of curcumin, even with robust plasma elimination mechanisms in place, the elimination of curcumin during infusion may be reaching saturation. Despite finding high levels of curcumin in patients, #3, #19 and #24, the plasma levels and pharmacokinetics of curcumin and THC for the remaining patients were clearly dose-dependent and displayed a moderate to high, but not an excessive amount of variability for such a diverse patient population.

Evaluation of antitumor activity was only a secondary study objective and tumor response according to RECIST v1.1 after 8 weeks was not expected in this heavily pre-treated patient population especially at low doses. Tumor marker response was observed in patient #27 with prostate carcinoma and bone and lymph node metastases and lymphangiosis of the lung and in patient #30 with colon carcinoma and liver and lung metastases were objective signs of efficacy. Additionally transient clinical benefit was reported by the investigator in both patients. Previous treatments for patient #27 were radiation therapy and six prior chemotherapy combinations. Patient #30 had already received seven prior chemotherapy combinations. Interestingly Hb in these two patients was rather constant compared to other patients at this dose level who showed more reduction of Hb during the infusions.

In general, patients recruited into this study had failed previous anti-cancer treatments and exhibited often an aggressive course of disease. Not wishing to be bound by theory, it might be that curcumin's ability to kill cancer stem cells was not translated into tumor shrinkage due to the limited treatment time and impairment of immunological function. It is possible, that the ideal role of liposomal curcumin as an anti-cancer agent should be in combination with other chemotherapies in earlier treatment lines. The activity of curcumin as a sphingosine kinase inhibitor also suggests it may help in reducing the chances of recurrence in patients who have responded to other anti-neoplastic agents[30].

Study Drug. Curcumin, (1E6E) -1,7- bis (4 hydroxy-3-methoxyphenyl) -1,6-heptadiene-3,5 dione, molecular weight 368.38 g/mol, was synthesized at Sami Labs Limited (Bangalore, India) under Good Manufacturing Practice (GMP) with a purity of 99.2%. Liposomal curcumin was manufactured, tested, packaged and labeled by Polymun Scientific, Austria in compliance with GMP as described for a previous phase I study[23]. Final batch release was done by Polymun's QP. Liposomal curcumin was provided in 20 ml glass vials containing 20 ml liposomal suspension with a curcumin concentration of 6.0±1.5 mg/ml.

Patients. Eligible to this study were male and female patients ≥18 years with a histologically/cytologically confirmed diagnosis of locally advanced or metastatic cancer, for whom no anti-tumor therapy of proven benefit was available at study enrolment. Other key inclusion criteria were ECOG 0-2, life expectancy of at least 3 months, at least one measurable lesion according RECIST v1.1, absolute neutrophil count ≥1500 cells/μL, Hb>9.5 g/dL and a platelet count>100,000 μL, renal function>50 mL/min with estimated creatinine clearance (eCcr) using the Cockcroft-Gault formula or serum creatinine<1.5 mg/dL, total serum bilirubin<3.0 mg/dL, and AST and ALT less than 5 times the upper limit of normal (ULN) and signed informed consent. Patients with lymphoma, hematological cancer or glioblastoma multiforme were excluded from this study. Other key exclusion criteria were active infection, or a fever>38.5 ° C. within three days prior to the first day of study drug dosing, evidence of disease (hemolytic diathesis, hemochromatosis) that could be exacerbated by administering liposomal curcumin, currently on any medications classified as cytochrome p450 inhibitors or inducers, systemic therapy less than three weeks before the day of first study treatment, unresolved toxicities from prior systemic anti-cancer therapy except symptomatic motor or sensory neuro-toxicities NCI-CTC Grade≤2, clinically significant ECG aberrations according to the discretion of the investigator, left ventricular ejection fraction (LVEF)<50%, NYHA Class 2 or congestive heart failure, uncontrolled hypertension, or cardiac arrhythmias, known positive HIV serology or evidence of active hepatitis. Women who are pregnant, breast feeding, and not taking contraceptive measures were also excluded from study participation.

The study was conducted at the IIIrd Medical Department of the Paracelsus Medical University Salzburg and the Salzburg Cancer Research Institute. The study protocol was approved by the Ethics Committee of the province Salzburg (Clinicaltrials.gov identifier NCT02138955, European Clinical Trials Database [EudraCT] number 2013-001594-24). The study was conducted in accordance with the Declaration of Helsinki, Good Clinical Practice guidelines, and all local and federal regulations. All patients provided written informed consent.

Study design and dose escalation. This was an open-label, single center, dose escalation study. Study medication was given once per week (+/−1 day). On each day of treatment, patients were pre-medicated with 50 mg diphenhydramine and received an intravenous infusion of liposomal curcumin. Individual patients received treatment on study until the completion of 8 cycles (8 weeks), until tumor progression or intolerable toxicity, whichever came first. If on week 8 the patients exhibited objective clinical benefit, they could be offered the option of additional liposomal curcumin at the same dose and schedule they previously received.

The starting dose of 120 mg/m² over 24 h was based on the results in the Phase 1a safety study in healthy subjects. After 2 infusions in the first patient the study was temporarily interrupted due to precipitate formation in the infusion line. The patient did not experience any adverse events related to this incident. After extensive in-use stability tests a substantial amendment was filed with regulatory authorities and the concerned EC and the study was restarted in the first cohort of three patients with infusions of eight hour duration at a DL of 100 mg/m² liposomal curcumin. Dose escalation to the next DL was permitted if no DLT occurred during the first three weeks in three evaluable patients and the DSMB recommended dose escalation.

Safety assessments. Safety assessments included monitoring and recording all AEs, serious adverse events (SAE), the regular monitoring of hematology, blood chemistry, regular physical examinations and measurement of vital signs.

DLT were defined as Hemolysis (NCI-CTC grade 2: Evidence of hemolysis and ≥2 grams decrease in Hb in 2 consecutive measurements within 120 min after the end of infusion, confirmation of a causal relationship to the study medication according to the investigator), NCI-CTC Grade 3 or 4 toxicity, excluding nausea and vomiting, which responds to antiemetic treatment and alopecia, prolonged (>2 weeks) NCI-CTC Grade 2 toxicities (neurocerebellar:Intention tremor, slurred speech, nystagmus, dysmetria), NCI-CTC Grade 4 platelet toxicities, NCI-CTC Grade 4 granulocyte toxicity ≥7 days, and febrile neutropenia: defined as an absolute neutrophils count <500/mm$^3$ and fever either as 2 elevations of oral temperature >38° C. with one hour interval or a single oral temperature, >38.5° C., provided that this single episode is not clearly related to other events.

Pharmacokinetic assessments. Blood samples were collected into $K_3$-EDTA containing tubes for the determination of curcumin and THC plasma concentration by liquid chromatographic-tandem mass spectrometric method using a validated method at Nucro Technics (Canada) as previously reported for a study with liposomal curcumin [23]. Samples for infusion #1 were collected at baseline (BL), 2 h after start of infusion and after end of infusion at 0 min =EOI, 10 min, 20 min, 30 min, 45 min, 60 min and 120 min and at EOI for infusions #2, #3, #5 and #8. A preliminary PK analysis of the samples obtained from patients treated in dose level 2 that was requested by the safety data monitoring board revealed that curcumin plasma levels were only detectable during infusion (at 2 h) but not after the end of infusion. To allow better characterization of the pharmacokinetics of curcumin in plasma the samples collection time points were adapted (Amendment 3, starting from patient #17) to BL, 2 h, 4 h and 6 h during infusion and EOI, 10 min, 20 min, 30 min and 45 min after EOI. The number of blood collections remained unchanged.

The PK analysis focused on patients who included into the study after amendment 3 and had enough curcumin plasma concentration values above the limit of quantitation (LoQ=10 ng/ml). These patients had received 150, 190, 240, or 300 mg/m$^2$ doses of curcumin over 8 hours of infusion or received 300 mg/m$^2$ over 6 hours of infusion. Due to a lack of concentration data following infusion for the majority of patients, the pharmacokinetic parameters determined were $C_{max}$, $T_{max}$, $AUC_{0-Tlast}$ and $C_{last}$ using the validated Phoenix WinNonlin Professional Software, (v6.3).

Dose proportionality and linearity was assessed using the plasma concentrations of curcumin determined at 2 h during infusion compared to the rate of infusion and linear regression of the plot of infusion rate versus 2 h plasma concentration of curcumin. The rate of infusion was used instead of the dose of curcumin to compare data over different infusion times.

Efficacy assessments. Efficacy endpoints were the response rate (complete response/partial response/stable disease/progressive disease) according to RECIST v1.1 after 8 weeks, of monitoring of serum cancer markers and clinical signs and symptoms of cancer.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Khor T O, Keum Y S, Lin W, Kim J H, Hu R, Shen G et al. Combined inhibitory effects of curcumin and phenethyl isothiocyanate on the growth of human PC-3 prostate xenografts in immunodeficient mice. Cancer Res 2006; 66: 613-621.

Meskin M S, Bidlack W R, Davies A J, Lewis D S, Randolph R K. Phytochemicals: Mechanisms of Action. CRC Press: Boca Raton, Fla., 2003.

Chainani-Wu N. Safety and anti-inflammatory activity of curcumin: a component of turmeric (Curcuma longa). J Altern Complement Med 2003; 9: 161-168.

Di Pierro F, Settembre R. Safety and efficacy of an add-on therapy with curcumin phytosome and piperine and/or lipoic acid in subjects with a diagnosis of peripheral neuropathy treated with dexibuprofen. J Pain Res 2013; 6: 497-503.

Kanai M, Otsuka Y, Otsuka K, Sato M, Nishimura T, Mori Y et al. A phase I study investigating the safety and pharmacokinetics of highly bioavailable curcumin (Theracurmin®) in cancer patients. Cancer Chemother Pharmacol 2013; 71: 1521-1530.

Kunwar A, Bank A, Mishra B, Rathinasamy K, Pandey R, Priyadarsini K I. Quantitative cellular uptake, localization and cytotoxicity of curcumin in normal and tumor cells. Biochim Biophys Acta-General Subjects 2008; 1780: 673-679.

Bolger G T, Licollari A, Tan A, Greil R, Vcelar B, Majeed M et al. Distribution and metabolism of Lipocurc™(liposomal curcumin) in dog and human blood cells: species selectivity and pharmacokinetic relevance. Anticancer Res 2017; 37: 3483-3492.

Sordillo P P, Helson L. Curcumin and cancer stem cells: curcumin has asymmetrical effects on cancer and normal stem cells. Anticancer Res 2015; 35: 599-614.

Chen F, Wang H, Xiang X, Yuan J, Chu W, Xue X et al. Curcumin increased the differentiation rate of neurons in neural stem cells via wnt signaling in vitro study. J Surg Res 2014; 192: 298-304.

Tiwari S K, Agarwal S, Seth B, Yadav A, Nair S, Bhatnagar P et al. Curcumin-loaded nanoparticles potently induce adult neurogenesis and reverse cognitive deficits in Alzheimer's disease model via canonical Wnt/β-catenin pathway. ACS Nano 2013; 8: 76-103.

Chang Y C, Chang W C, Hung K H, Yang D M, Cheng Y H, Liao Y W et al. The generation of induced pluripotent stem cells for macular degeneration as a drug screening platform: identification of curcumin as a protective agent for retinal pigment epithelial cells against oxidative stress. Front Aging Neurosci 2014; 6: 191.

Aziza S A, Abdel-Aal S A, Mady H A. Chemopreventive effect of curcumin on oxidative stress, antioxidant status, DNA fragmentation and caspase-9 gene expression in 1, 2-dimethylhydrazine-induced colon cancer in rats. American J Biochem Mol Biol 2014; 4: 22-34.

Hua W M, Liang Z Q, Fang Y, Gu Z L, Guo C Y. Mechanisms of curcumin protecting endothelial cells against ischemia and reperfusion injury. Chinese Pharmacol Bull 2009; 8: 13.

Han J, Pan X Y, Xu Y, Xiao Y, An Y, Tie L et al. Curcumin induces autophagy to protect vascular endothelial cell survival from oxidative stress damage. Autophagy 2012, 8: 812-825.

Xu Y, Ku B, Cui L, Li X, Barish P A, Foster T C et al. Curcumin reverses impaired hippocampal neurogenesis and increases serotonin receptor 1A mRNA and brain-derived neurotrophic factor expression in chronically stressed rats. Brain Res 2007; 1162: 9-18.

Wang Y J, Pan M H, Cheng A L, Lin L I, Ho Y S, Hsieh C Y et al. Stability of curcumin in buffer solutions and characterization of its degradation products. J Pharm Biomed Anal 1997; 15: 1867-1876.

Sharma R A, Steward W P, Gescher AJ. Pharmacokinetics and pharmacodynamics of curcumin. In: Aggarwal BB, Surh Y, Shishodia S (eds). The molecular targets and therapeutic uses of curcumin in health and disease. Springer: Boston, Mass., USA, 2007, pp. 453-470.

Li L, Braiteh FS, Kurzrock R. Liposome-encapsulated curcumin: in vitro and in vivo effects on proliferation, apoptosis, signaling, and angiogenesis. Cancer 2005; 104: 1322-1331.

Li L, Ahmed B, Mehta K, Kurzrock R. Liposomal curcumin with and without oxaliplatin: effects on cell growth, apoptosis, and angiogenesis in colorectal cancer. Mol Cancer Ther 2007; 6: 1276-1282.

Mach C M, Mathew L, Mosley S A, Kurzrock R, Smith J A. Determination of minimum effective dose and optimal dosing schedule for liposomal curcumin in a xenograft human pancreatic cancer model. Anticancer Res 2009; 29: 1895-1899.

Helson L, Bolger G, Majeed M, Vcelar B, Pucaj K, Matabudul D. Infusion pharmacokinetics of LipocurcTM (liposomal curcumin) and its metabolite tetrahydrocurcumin in Beagle dogs. Anticancer Res 2012; 32: 4365-4370.

Ranjan A P, Mukerjee A, Helson L, Gupta R, Vishwanatha J K. Efficacy of liposomal curcumin in a human pancreatic tumor xenograft model: inhibition of tumor growth and angiogenesis. Anticancer Res 2013; 33: 3603-3609.

Storka A, Vcelar B, Klickovic U, Gouya G, Weisshaar S, Aschauer S et al. Safety, tolerability and pharmacokinetics of liposomal curcumin (Lipocurc™) in healthy humans. Int J Clin Pharmacol Therapeut 2015; 53: 54-65.

Matabudul D, Pucaj K, Bolger G, Vcelar B, Majeed M, Helson L. Tissue distribution of (Lipocurc™) liposomal curcumin and tetrahydrocurcumin following two-and eight-hour infusions in beagle dogs. Anticancer Res 2012; 32: 4359-4364.

Manrique-Moreno M, Villena F, Sotomayor CP, Edwards AM, Munoz MA, Garidel P et al. Human cells and cell membrane molecular models are affected in vitro by the nonsteroidal anti-inflammatory drug ibuprofen. Biochim Biophys Acta -Biomembranes 2011; 1808: 2656-2664.

Pierce A, Nester T. Pathology consultation on drug-induced hemolytic anemia. Am J Clin Pathol 2011; 136: 7-12.

Perkins J. Fatal drug-induced immune hemolytic anemia due to cefotetan; A case study. Asian J Transfu Sci 2008; 2: 20-23.

Barbaryan A, Iyinagoro C, Nwankwo N, Ali A M, Saba R, Kwatra S G, et al. Ibuprofen-induced hemolytic anemia. Case Rep Hematol 2013; 142865: 1-3.

Storka A, Vcelar B, Klickovic U, Gouya G, Weisshaar S, Aschauer S, et al. Effect of liposomal curcumin on red blood cells in vitro. Anticancer Res 2013; 33: 3629-3634.

Sordillo L A, Sordillo P P, Helson L. Sphingosine kinase inhibitors as maintenance therapy of glioblastoma after ceramide-induced response. Anticancer Res 2016; 36: 2085-2095.

What is claimed:

1. A method of treating a proliferative disorder comprising administering a therapeutically effective amount of an intravenous liposomal curcumin or curcuminoids to a human subject in need thereof in accordance with a dosing regimen comprising: at least one treatment cycle administering the therapeutically effective amount of the liposomal curcumin or curcuminoids of at least 125 mg/m² over 3, 4, 5, 6, 7, or 8 hours or less, wherein the treatment cycle is followed by a rest period of 4, 5, 6, or 7 days during which no liposomes or active agent are administered, and wherein the treatment cycle is repeated for 2, 3, 4, 5, 6, 7, 8, 9, 10, 11, or 12 consectuive weeks.

2. The method of claim 1, wherein the liposomal curcumin or curcuminoids are administered at a dose of 150, 200, 250, 300, 350, 400, 450, 500, or 600 mg/m²; wherein the liposomal curcumin or curcuminoids are administered at a dose of 125 to 600 mg/m², over 3 to 6 hours; wherein the liposomal curcumin or curcuminoids are administered at a dose of 300 to 600 mg/m², over 3 to 4 hours; wherein the liposomal curcumin or curcuminoids are administered at a dose of 300 to 600 mg/m², over 3 to 8 hours.

3. The method of claim 1, wherein the liposomal curcumin or curcuminoids is administered at a dose of at least 300 mg/m² over 3, 4, 5, 6, 7, or 8 hours.

4. The method of claim 1, further comprising providing an effective dose of at least one of: irinotecan, 5-fluorouracil, leucovorin, capecitabine, anthracyclins, doxorubicin, dasatinib, itnatinib mesylate, lapatinib, nilotinib, sorafenib, sunitinib, trastuzumab, alemtuzumab, bevacizumab, cetuximab, gemtuzumab, panitumumab, rituximab, tositumomab, trastuzumab and combinations thereof.

5. The method of claim 1, wherein the proliferative disease is a metastatic cancer, or wherein the proliferative disease is selected from breast, uterine, cervical, brain, colon, leukemia, cervix, prostate, GI tract, hepatic, melanoma, or pancreatic cancer.

6. The method of claim 1, wherein the liposome comprises 1,2-ditnyristoyl-sn-glycero-3-phosphocholine (DMPC), 1,2-Dimyristoyl-sn-glycero-3-phosphorylglycerol (DMPG), or DMPC/DMPG lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine.

7. The method of claim 1, wherein the liposome treats pericardial fibrosis, endomyocardial fibrosis, heart failure, hemorrhagic myocardial necrosis, cardiomyopathy, myocarditis, acute coronary disease, hypertension, myocardial infarction, QT prolongation, or pericarditis caused by the curcumin or curcuminoids.

8. The method of claim 1, wherein the liposome does not encapsulate the active agent.

9. The method of claim 1, wherein the liposomal curcumin or curcuminoids are a curcumin/curcurninoid:liposome complex, wherein the curcumin comprises between 2 to 9 weight percent of the curcumin/curcuminoid:liposome complex, wherein the curcumin is at least one of natural or synthetic curcumin and wherein the curcumin/curcuminoid:liposome complex has a molar ratio of curcumin to lipid of 1:7.5 to 1:10, wherein the lipid combination is selected from: DMPC; DMPC:Chol 9:1; DMPC:DMPG 9:1.; DMPC:Chol:DMPG 8:1:1; DPPC:DMPG 9:1; DPPC:Chol:DMPG 8:1:1; DMPC:DSPE-PEG-2000 95:5; DMPC:Chol:DSPE-PEG-2000 90:10:05; DMPC/DMPG 7:3; DPPC/DMPG 7:3; DPPC/DMPG 9:1.

10. The method of claim 1, wherein the liposomal curcumin or curcuminoids are a curcumin/curcuminoid:liposome complex, wherein the curcumin comprises between 2 to 9 weight percent of the curcumin/curcuminoid:liposome complex, wherein the curcumin is at least one of natural or synthetic curcumin and wherein the curcumin/curcuminoid:liposome complex has a weight to weight ratio of curcumin to lipid of 1:7.5 to 1:10, wherein the lipid combination is selected from: DMPC; DMPC:Chol 9:1; DMPC:DMPG 9:1; DMPC:Chol:DMPG 8:1:1; DPPC:DMPG 9:1; DPPC:Chol:DMPG 8:1:1; DMPC:DSPE-PEG-2000 95:5; DMPC:Chol:DSPE-PEG-2000 90:10:05; DMPC/DMPG 7:3; DPPC/DMPG 7:3; DPPC/DMPG 9:1.

* * * * *